United States Patent [19]

Janssens et al.

[11] Patent Number: 5,272,150

[45] Date of Patent: Dec. 21, 1993

[54] HYDROXYALKYLFURANYL DERIVATIVES

[75] Inventors: Frans E. Janssens, Bonheiden; Gaston S. M. Diels, Ravels; Joseph E. Leenaerts, Hoogstraten, all of Belgium

[73] Assignee: Janssen Pharmaceutica N.V., Beerse, Belgium

[21] Appl. No.: 842,024

[22] Filed: Feb. 26, 1992

Related U.S. Application Data

[63] Continuation of Ser. No. 488,566, Mar. 5, 1990, abandoned, which is a continuation-in-part of Ser. No. 335,022, Apr. 7, 1989, abandoned.

[51] Int. Cl.5 .................. A61K 31/415; C07D 239/00
[52] U.S. Cl. ..................................... 514/258; 514/259; 540/603; 544/278; 544/282
[58] Field of Search ................ 540/603; 544/278, 282; 514/258, 259

[56] References Cited

U.S. PATENT DOCUMENTS

| | | | |
|---|---|---|---|
| 4,556,660 | 12/1985 | Janssens et al. | 514/272 |
| 4,588,722 | 5/1986 | Janssens et al. | 514/228 |
| 4,695,569 | 9/1987 | Janssens | 544/282 |
| 4,695,575 | 9/1987 | Janssens et al. | 514/322 |
| 4,835,161 | 5/1989 | Janssens et al. | 514/303 |
| 4,897,401 | 1/1990 | Janssens et al. | 514/303 |
| 4,988,689 | 1/1991 | Janssens et al. | 514/212 |
| 5,041,448 | 8/1991 | Janssens et al. | 514/266 |

Primary Examiner—Marianne M. Cintins
Assistant Examiner—Catherine S. Kilby Scalzo
Attorney, Agent, or Firm—Charles J. Metz

[57] ABSTRACT

Hydroxyalkylfuranyl derivatives, the pharmaceutically acceptable acid addition salts and stereochemically isomeric forms thereof having antiallergic properties, compositions containing the same and methods of treating warm-blooded animals suffering from allergic diseases.

6 Claims, No Drawings

HYDROXYALKYLFURANYL DERIVATIVES

CROSS-REFERENCE TO RELATED APPLICATION

This application is a continuation of our copending application Ser. No. 488,566, filed Mar. 5, 1990, (now abandoned) which in turn was a continuation-in-part of application Ser. No. 335,022, filed Apr. 7, 1989, now abandoned.

BACKGROUND OF THE INVENTION

In U.S. Pat. Nos. 4,556,660; 4,634,704; 4,695,569; 4,695,575; 4,588,722; 4,835,161; 4,897,401 and in EP-A-0,206,415 and 0,297,661 there are disclosed related furanyl and/or alkylfuranyl derivatives as antihistaminics and serotonin antagonists.

DESCRIPTION OF THE INVENTION

The present invention is concerned with compounds having the formula

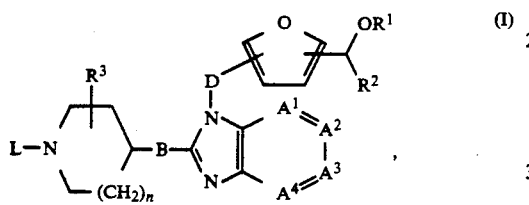

the pharmaceutically acceptable acid addition salts and the stereochemically isomeric forms thereof, wherein $-A^1=A^2-A^3=A^4-$ is a bivalent radical having the formula $-CH=CH-CH=CH-$ (a-1), $-N=CH-CH=CH-$ (a-2), $-CH=N-CH=CH-$ (a-3), $-CH=CH-N=CH-$ (a-4), $-CH=CH-CH=N-$ (a-5), $-N=CH-N=CH-$ (a-6)

or $-CH=N-CH=N-$ (a-7), wherein one or two hydrogen atoms in said radicals (a-1) to (a-7) each independently from one another may be replaced by halo, $C_{1-6}$alkyl, $C_{1-6}$alkyloxy, trifluoromethyl or hydroxy;

D is $C_{1-4}$alkanediyl;

$R^1$ is hydrogen, $C_{1-6}$alkyl, aryl$C_{1-6}$alkyl or $C_{1-6}$alkylcarbonyl;

$R^2$ is hydrogen or $C_{1-6}$alkyl;

$R^3$ is hydrogen or $C_{1-6}$alkyl;

n is 0, 1 or 2;

B is $NR^4$, O, S, SO, $SO_2$ or $CH_2$;

$R^4$ is hydrogen, $C_{1-6}$alkyl, $C_{3-6}$cycloalkyl or aryl$C_{1-6}$alkyl;

L is hydrogen, $C_{1-12}$alkyl, $C_{3-6}$cycloalkyl, $C_{3-6}$alkenyl optionally substituted with aryl, $C_{1-6}$alkylcarbonyl, $C_{1-6}$alkyloxycarbonyl, arylcarbonyl, aryl$C_{1-6}$alkyloxycarbonyl, $C_{1-6}$alkylsulfonyl, arylsulfonyl, or a radical of formula $-Alk-R^5$ (b-1), $-Alk-Y-R^6$ (b-2), $-Alk-Z^1-C(=X)-Z^2-R^7$ (b-3), or $-CH_2-CHOH-CH_2-O-R^8$ (b-4)

wherein $R^5$ is halo, cyano, isocyanato, isothiocyanato, aryl, Het or arylsulfonyl;

$R^6$ is hydrogen, aryl, Het or $C_{1-6}$alkyl optionally substituted with halo, aryl or Het;

$R^7$ is hydrogen, aryl, Het or $C_{1-6}$alkyl optionally substituted with halo, aryl or Het;

$R^8$ is aryl or naphthalenyl;

Y is O, S, $NR^9$; said $R^9$ being hydrogen, $C_{1-6}$alkyl or $C_{1-6}$alkylcarbonyl;

$Z^1$ and $Z^2$ each independently are O, S, $NR^{10}$ or a direct bond;

said $R^{10}$ being hydrogen or $C_{1-6}$alkyl;

X is O, S or $NR^{11}$; said $R^{11}$ being hydrogen, $C_{1-6}$alkyl or cyano;

each Alk independently is $C_{1-6}$alkanediyl;

each Het is a five- or six-membered heterocyclic ring containing 1, 2, 3 or 4 hetero-atoms selected from oxygen, sulfur and nitrogen, provided that no more than 2 oxygen and/or sulfur atoms are present, said five or six-membered ring being optionally condensed with a five- or six-membered carbocyclic or heterocyclic ring also containing 1, 2, 3 or 4 heteroatoms selected from oxygen, sulfur and nitrogen, provided that the latter ring does not contain more than 2 oxygen and/or sulfur atoms and that the total number of heteroatoms in the bicyclic ring system is less than 6; and when Het is a monocyclic ring system it may optionally be substituted with up to 4 substituents, when Het is a bicyclic ring system it may optionally be substituted with up to 6 substituents, said substituents being selected from a bivalent radical of formula X; halo; isocyanato; isothiocyanato; nitro; cyano; trifluoromethyl; a radical of formula $-E$; a radical of formula $-Y-E$; or a radical of formula $-Z^1-C(=X)-Z^2-E$; wherein X, Y, $Z^1$ and $Z^2$ are as previously defined hereinabove; and E is hydrogen, aryl or $C_{1-6}$alkyl being optionally substituted with aryl, $C_{1-6}$alkyloxy, aryloxy, hydroxy or $C_{1-6}$alkyloxycarbonyl; and each aryl is phenyl optionally substituted with 1, 2 or 3 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl;

provided that when $R^5$ is Het, said Het is other than a 2-amino-3,4-dihydro-4-oxo-5-pyrimidinyl group, wherein the hydrogen on the 6-position may be replaced by a $C_{1-6}$alkyl radical and wherein the nitrogen atom in the 3-position and the nitrogen atom of the amino group optionally are substituted, or are linked by a bivalent radical of formula $-(CH_2)_2-$, $-(CH_2)_3-$, $-CH=CH-$, $-CH=N-$, $-N=CH-$, or $-N=CH-CH_2-$, wherein one or where possible two hydrogen atoms of said bivalent radicals each independently from one another may be replaced by $C_{1-6}$alkyl.

In the compounds of formula (I) where $R^5$, $R^6$ or $R^7$ is Het, said Het may be partly or completely saturated, or unsaturated. The compounds of formula (I) wherein Het is partly saturated or unsaturated and is substituted with hydroxy, mercapto or amino, may also exist in their tautomeric forms. Such forms although not explicitly indicated hereinabove, are intended to be included within the scope of the invention.

As used in the foregoing definitions halo is generic to fluoro, chloro, bromo and iodo; $C_{1-6}$alkyl defines straight and branch chained saturated hydrocarbon radicals having from 1 to 6 carbon atoms such as, for example, methyl, ethyl, propyl, 1-methylethyl, butyl, 1,1-dimethylethyl, 1-methylpropyl, 2-methylpropyl, pentyl, hexyl and the like; $C_{1-12}$alkyl defines $C_{1-6}$alkyl radicals as defined hereinabove and the higher homologs thereof having from 7 to 12 carbon atoms; $C_{3-6}$cycloalkyl is generic to cyclopropyl, cyclobutyl, cyclopentyl and cyclohexyl; $C_{3-6}$alkenyl defines straight and branch chained hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like, the carbon atom of said $C_{3-6}$alkenyl connected to a heteroatom preferably being saturated; $C_{1-4}$alkanediyl defines bivalent straight and branch chained saturated hydrocarbon radicals having from 1 to 4 carbon atoms such as, for example, methylene, 1,2-ethanediyl, 1,3-propanediyl, 1,4-butanediyl and the branched isomers thereof; $C_{1-6}$alkanediyl defines $C_{1-4}$alkanediyl radicals as defined hereinabove and the higher homologs thereof having from 5 to 6 carbon atoms such as, for example, 1,5-pentanediyl, 1,6-hexanediyl and the branched isomers thereof.

Said pharmaceutically acceptable acid addition salts as mentioned hereinabove comprise the therapeutically active non-toxic acid addition salt forms which the compounds of formula (I) are able to form. Said salt forms can conveniently be obtained by treating the base form of the compounds of formula (I) with appropriate acids such as inorganic acids, for example, hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butanedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term acid addition salt also comprises the hydrates and solvent addition forms which the compounds of formula (I) are able to form. Examples of such forms are e.g. hydrates, alcoholates and the like.

The compounds of this invention may have several asymmetric carbon atoms in their structure. Each of these chiral centers may be indicated by the stereochemical descriptors R and S, this R and S notation corresponding to the rules described in Pure Appl. Chem., 1976, 45, 11-30.

Pure stereochemically isomeric forms of the compounds of formula (I) may be obtained by the application of art-known procedures. Diastereoisomers may be separated by physical methods such as selective crystallization and chromatographic techniques, e.g. counter current distribution, liquid chromatography and the like; and enantiomers may be separated from each other following art-known resolution methods, for example, by the selective crystallization of their diastereomeric salts with chiral acids. Pure stereochemically isomeric forms may also be derived from the corresponding pure stereochemically isomeric forms of the appropriate starting materials, provided that the reactions occur stereospecifically. Preferably, if a specific stereoisomer is desired, said compound will be synthesized by stereoselective methods of preparation. These methods will advantageously employ enantiomerically pure starting materials. Stereochemically isomeric forms of the compounds of formula (I) are obviously intended to be included within the scope of the invention.

The moiety

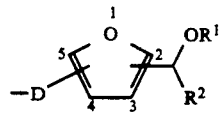

in the compounds of formula (I) as defined hereinabove, in particular is (2—CHR$^2$OR$^1$—furan-5-yl)—C$_{1-4}$alkyl—, (2—CHR$^2$OR$^1$—furan-4-yl)—C$_{1-4}$alkyl—, (2—CHR$^2$OR$^1$—furan-3-yl)—C$_{1-4}$alkyl—, (3—CHR$^2$OR$^1$—furan-5-yl)—C$_{1-4}$alkyl—, (3—CHR$^2$OR$^1$—furan-4-yl)—C$_{1-4}$alkyl— or (3—CHR$^2$OR$^1$—furan-2-yl)—C$_{1-4}$alkyl—, wherein R$^1$ and R$^2$ are as defined hereinabove and C$_{1-4}$alkyl defines straight and branch chained hydrocarbon radicals having from 1 to 4 carbon atoms i.e. methyl, ethyl, propyl, methylethyl, butyl, 1-methylpropyl, 2-methylpropyl and 1,1-dimethylethyl.

In particular, the radical Het as defined hereinabove may be:

(i) an optionally substituted five- or six-membered heterocyclic ring containing 1, 2, 3 or 4 heteroatoms selected from oxygen, sulfur and nitrogen, provided that no more than 2 oxygen and/or sulfur atoms are present;

(ii) an optionally substituted five- or six-membered heterocyclic ring containing 1 or 2 heteroatoms selected from oxygen, sulfur and nitrogen, being fused with an optionally substituted five- or six-membered ring through 2 carbon atoms or 1 carbon and 1 nitrogen atom, containing in the remainder of the fused ring only carbon atoms; or (iii) an optionally substituted five- or six-membered heterocyclic ring containing 1 or 2 heteroatoms selected from oxygen, sulfur and nitrogen, being fused with an optionally substituted five- or six-membered heterocyclic ring through 2 carbon atoms or 1 carbon and 1 nitrogen atom, containing in the remainder of the fused ring 1 or 2 heteroatoms selected from oxygen, sulfur and nitrogen;

wherein Het being a monocyclic ring system may be optionally substituted with up to 4 substituents; and wherein Het being a bicyclic ring system may be optionally substituted with up to 6 substituents, said substituents being the same as defined hereinabove.

More particularly Het is selected from pyridinyl, optionally substituted with one or two substituents each independently selected from halo, amino, mono- and di($C_{1-6}$alkyl)amino, aryl$C_{1-6}$alkylamino, nitro, cyano, aminocarbonyl, $C_{1-6}$alkyl, $C_{1-6}$alkyloxy, $C_{1-6}$alkylthio, $C_{1-6}$alkyloxycarbonyl, hydroxy, $C_{1-6}$alkylcarbonyloxy, aryl$C_{1-6}$alkyl and carboxyl; pyridinyloxide, optionally substituted with nitro; pyrimidinyl, optionally substituted with one or two substituents each independently selected from halo, amino, $C_{1-6}$alkylamino, aryl$C_{1-6}$alkylamino, hydroxy, $C_{1-6}$alkyl, $C_{1-6}$alkyloxy, $C_{1-6}$alkylthio and aryl$C_{1-6}$alkyl; pyridazinyl, optionally substituted with $C_{1-6}$alkyl or halo; pyrazinyl, optionally substituted with halo, amino or $C_{1-6}$alkyl; thienyl, optionally substituted with halo or $C_{1-6}$alkyl; furanyl, optionally substituted with halo or $C_{1-6}$alkyl; pyrrolyl, optionally substituted with $C_{1-6}$alkyl; thiazolyl, optionally substituted with $C_{1-6}$alkyl, $C_{1-6}$alkyloxycarbonyl, aryl or aryl$C_{1-6}$alkyl; imidazolyl, optionally substituted with one or two substituents each independently selected from $C_{1-6}$alkyl, aryl$C_{1-6}$alkyl and nitro; tetrazolyl, optionally substituted with $C_{1-6}$alkyl; 1,3,4-thiadiazolyl, optionally substituted with $C_{1-6}$alkyl; 5,6-dihydro-4H-1,3-thiazin-2-yl, optionally substituted with $C_{1-6}$alkyl; 4,5-dihydrothiazolyl, optionally substituted with $C_{1-6}$alkyl; oxazolyl, optionally substituted with $C_{1-6}$alkyl; 4,5-dihydro-5-oxo-1H-tetrazolyl, optionally substituted with $C_{1-6}$alkyl; 1,4-dihydro-2,4-dioxo-3(2H)-pyrimidinyl, optionally substituted with $C_{1-6}$alkyl; 4,5-dihydro-4-oxopyrimidinyl, optionally substituted with up to 3 substituents selected from $C_{1-6}$alkyl, amino, $C_{1-6}$alkylaminocarbonylamino, arylaminocarbonylamino, aryl$C_{1-6}$alkylamino and $C_{1-6}$alkylamino; 2,3-dihydro-3-oxopyridazinyl; 2-oxo-3-oxazolidinyl; pyrrolidinyl; piperidinyl; morfolinyl; thiomorfolinyl; dioxanyl, optionally substituted with $C_{1-6}$alkyl; indolyl, optionally substituted with hydroxy or $C_{1-6}$alkyl; quinolinyl, optionally substituted with hydroxy or $C_{1-6}$alkyl; quinazolinyl, optionally substituted with hydroxy or $C_{1-6}$alkyl; quinoxalinyl, optionally substituted with $C_{1-6}$alkyl; phthalazinyl, optionally substituted with halo; 1,3-dioxo-1H-isoindol-2(3H)-yl; 2,3-dihydro-3-oxo-4H-benzoxazinyl and 2,3-dihydro-1,4-benzodioxinyl, both being optionally substituted with $C_{1-6}$alkyl or halo; 2-oxo-2H-1-benzopyranyl and 4-oxo-4H-1-benzopyranyl, both being optionally substituted with $C_{1-6}$alkyl, and a bicyclic heterocyclic radical of formula

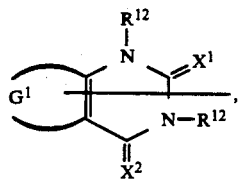  (c-1)

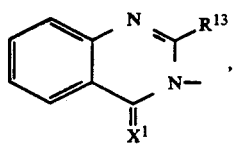  (c-2)

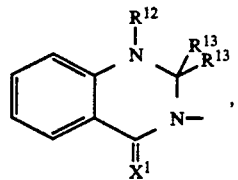  (c-3)

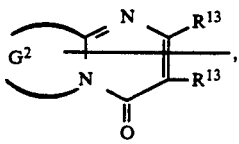  (c-4)

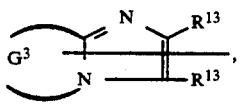  (c-5)

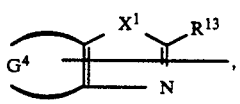  (c-6)

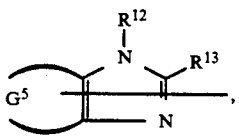  (c-7)

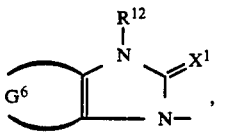  (c-8)

wherein $X^1$ and $X^2$ each independently are O or S;

each $R^{12}$ independently is hydrogen, $C_{1-6}$alkyl, aryl$C_{1-6}$alkyl, $C_{1-6}$alkyloxy-$C_{1-6}$alkyl, hydroxy$C_{1-6}$alkyl or $C_{1-6}$alkyloxycarbonyl;

each $R^{13}$ independently is hydrogen, $C_{1-6}$alkyl, hydroxy, mercapto, $C_{1-6}$alkyloxy, $C_{1-6}$alkylthio, halo or $C_{1-6}$alkyloxycarbonyl$C_{1-6}$alkyl;

and the long dash in the radicals (c-1), (c-4), (c-5), (c-6) and (c-7) signifies that any hydrogen atom of said radicals, including $R^{12}$ and $R^{13}$, may represent the bond linking Het to respectively Alk, Y or $Z^2$ in the radicals of formula (b-1), (b-2) and (b-3);

$G^1$ is —CH=CH—CH=CH— or —S—CH=CH—;

$G^2$ is —CH=CH—CH=CH—, —(CH$_2$)$_4$—, —S—(CH$_2$)$_2$—, S—(CH$_2$)$_3$—, —S—CH=CH—, —CH=CH—O—, —CH=C(CH$_3$)—O—, —NH—(CH$_2$)$_2$—, —NH—(CH$_2$)$_3$—, —NH—CH=CH—, —NH—N=CH—CH$_2$—, —NH—CH=N— or —NH—N=CH—;

$G^3$ is —CH=CH—CH=CH—, —CH$_2$—NH—(CH$_2$)$_2$—, —S—CH=CH—, —S—(CH$_2$)$_3$—, —N=CH—CH=CH—, —CH=N—CH=CH—, —CH=CH—N=CH—, —CH=CH—CH=N—, —N=CH—N=CH— or —CH=N—CH=N—;

$G^4$ is —CH=CH—CH=CH—, —CH$_2$—NH—(CH$_2$)$_2$—, —N=CH—CH=CH—, —CH=N—CH=CH—, —CH=CH—N=CH—, —CH=CH—CH=N—, —N=CH—N=CH— or —CH=N—CH=N—;

$G^5$ is —CH=CH—CH=CH—, —N=CH—CH=CH—, —CH=N—CH=CH—, —CH=CH—N=CH—, —CH=CH—CH=N—, —N=CH—N=CH— or —CH=N—CH=N—;

$G^6$ is —CH=CH—CH=CH—, —N=CH—CH=CH—, —CH=N—CH=CH—, —CH=CH—N=CH—, —CH=CH—CH=N—, —N=CH—N=CH— or —CH=N—CH=N—;

wherein one or two hydrogen atoms in said radicals $G^1$, $G^2$, $G^3$, $G^4$, $G^5$ or $G^6$ or in the benzene part of the radicals of formula (c-2) or (c-3) may be replaced by $C_{1-6}$alkyl, $C_{1-6}$alkylthio, $C_{1-6}$alkyloxy or halo when connected to a carbon atom; or by $C_{1-6}$alkyl, $C_{1-6}$alkyloxycarbonyl or aryl$C_{1-6}$alkyl when connected to a nitrogen atom.

Aryl as used in the definition of $R^1$, $R^5$, $R^6$ and $R^7$, in particular is phenyl optionally substituted with halo, $C_{1-6}$alkyl or $C_{1-6}$alkyloxy; aryl as used in the definition of $R^4$ and $R^8$ in particular is phenyl optionally substituted with halo.

A particular subgroup among the compounds of formula (I) comprises those compounds of formula (I) wherein $-A^1=A^2-A^3=A^4-$ is a bivalent radical of formula (a-1) or (a-2); another particular subgroup among the compounds of formula (I) comprises those compounds of formula (I) wherein $-A^1=A^2-A^3=A^4-$ is a bivalent radical having a formula (a-3) through (a-7).

Particularly interesting compounds are those compounds of the former subgroups wherein $R^1$ is hydrogen or aryl$C_{1-6}$alkyl; or $R^3$ is hydrogen; or B is NH or $CH_2$; or n is 1 or 2; or L is hydrogen, $C_{1-6}$alkyl, $C_{1-6}$alkylcarbonyl, $C_{1-6}$alkyloxycarbonyl, or a radical of formula (b-1), (b-2), (b-3) or (b-4); or the moiety

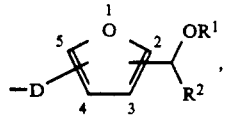

is (2-CHR$^2$OR$^1$-furan-5-yl)$C_{1-4}$alkyl or (3-CHR$^2$OR$^1$-furan-5-yl)-$C_{1-4}$alkyl; or several of these radicals have the meanings mentioned.

More particularly interesting compounds within the invention are those particularly interesting compounds of formula (I) wherein $R^1$ is hydrogen; or $R^2$ is hydrogen; or n is 1 or 2; or L is methyl or a radical of formula (b-1), (b-2) or (b-3); or $R^5$ is aryl or Het; or $R^6$ is $C_{1-6}$alkyl or Het; or $R^7$ is aryl, Het or $C_{1-6}$alkyl; or Y is O or NH; or $Z^1$ and $Z^2$ each independently are NR$^{10}$ or a direct bond, R$^{10}$ being hydrogen or $C_{1-6}$alkyl; or X is O; or each Alk is $C_{2-4}$alkanediyl; or Het is a more particular Het described hereinabove; or several of the radicals have the meanings mentioned.

The most interesting compounds are those more particularly interesting compounds wherein $R^5$ is phenyl optionally substituted with $C_{1-6}$alkyloxy; pyridinyl; 4,5-dihydro-5-oxo-1H-tetrazolyl; 2-oxo-3-oxazolidinyl; 2,3-dihydro-2-oxo-1H-benzimidazolyl; or a bicyclic radical of formula

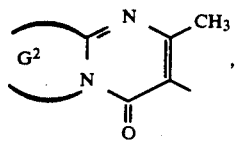

wherein $G^2$ is —CH=CH—CH=CH—, —S—(CH$_2$)$_3$—, —S—(CH$_2$)$_2$—, —S—CH=CH— or —CH=C(CH$_3$)—O—; or $R^6$ is $C_{1-6}$alkyl; pyridinyl optionally substituted with nitro, pyrimidinyl; pyrazinyl; pyridazinyl optionally substituted with halo; or 2,3-dihydro-3-oxopyridazinyl; or the radical (b-3) is (arylcarbonyl)$C_{1-6}$alkyl, $C_{1-6}$alkylaminocarbonyl$C_{1-6}$alkyl or a radical Het$^1$—C(=O)—NH—$C_{1-6}$alkyl wherein Het$^1$ is 1-methyl-1H-pyrrolyl, furanyl, thienyl or aminopyrazinyl.

In order to simplify the structural representation of some of the compounds and intermediates in the following preparations the moiety containing the imidazole group fused to a benzene, pyridine or pyrimidine ring will hereinafter be represented by the symbol Q.

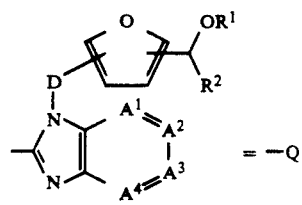

The compounds of formula (I) can generally be prepared by reacting an intermediate of formula (II) with an appropriately substituted diamine of formula (III).

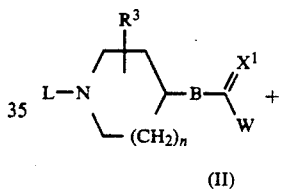

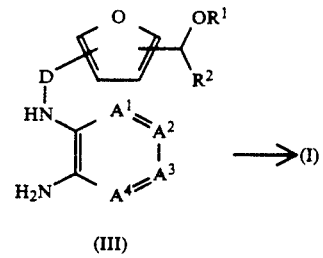

In this and the following reaction schemes W represents an appropriate reactive leaving group such as, for example, halo, e.g. chloro, bromo or iodo; $C_{1-6}$alkyloxy; $C_{1-6}$alkylthio, aryloxy or arylthio; and $X^1$ denotes O, S or NH.

The derivatives of formula (II) wherein B is CH$_2$ and W is halo may be generated in situ, for example, by halogenating the corresponding carboxylic acid with thionyl chloride, phosphorous trichloride, phosphoryl chloride, polyphosphoric acid and the like reagents. The reaction of (II) with (III) may be conducted in a suitable reaction-inert solvent such as, for example, a hydrocarbon, e.g., benzene, hexane and the like; an ether, e.g., 1,1'-oxybisethane, tetrahydrofuran and the like; a ketone, e.g., 2-propanone, 2-butanone and the like; an alcohol, e.g., methanol, ethanol, 2-propanol, 1-butanol and the like; a halogenated hydrocarbon, e.g., trichloromethane, dichloromethane and the like; an organic acid, e.g., acetic acid, propanoic acid and the like; a dipolar aprotic solvent e.g., N,N-dimethylformamide, N,N-dimethylacetamide and the like; or a mixture of such solvents. Depending upon the nature of the solvent and W it may be appropriate to add to the reaction mixture a base such as is commonly employed in the art of conducting N-alkylation reactions and/or a iodide salt such as an alkali metal iodide. Elevated temperatures and stirring may enhance the reaction rate. In some instances the reaction of (II) with (III) may first yield an intermediate of formula (II-a) which subsequently may be cyclized to the desired compound of formula (I), either in situ or, if desired, after isolation and purification.

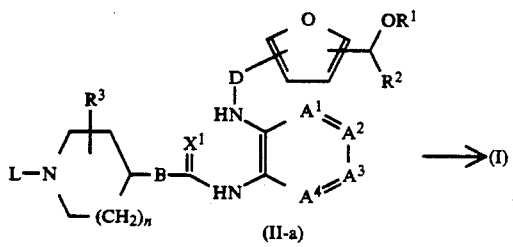

The compounds of formula (I) can also be prepared by reacting an intermediate of formula (IV) with an intermediate of formula (V) following art-known substitution reaction procedures. In (IV) and hereinafter, M is hydrogen when B is other than $CH_2$, or M represents an alkali or earth alkaline metal such as, for example, lithium or magnesium, when B represents $CH_2$.

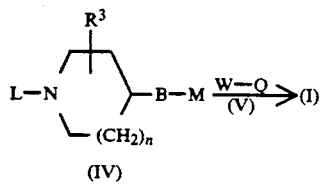

Similarly, the compounds of formula (I) can also be prepared by reacting an intermediate of formula (VI) with an intermediate of formula (VII) wherein M has the previously defined meaning. In formula (VI) and hereinafter $W^1$ represents an appropriate leaving group such as, for example, halo, e.g., chloro, bromo and the like; or a sulfonyloxy group such as, for example, methanesulfonyloxy, 4-methylbenzenesulfonyloxy and the like.

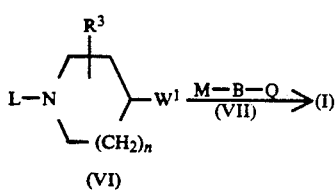

The compounds of formula (I) wherein B is —$CH_2$—, said compounds being represented by formula (I-a), can also be prepared by reacting an intermediate of formula (VIII) with an intermediate of formula (IX) or alternatively, by reacting an intermediate of formula (X) with an intermediate of formula (XI).

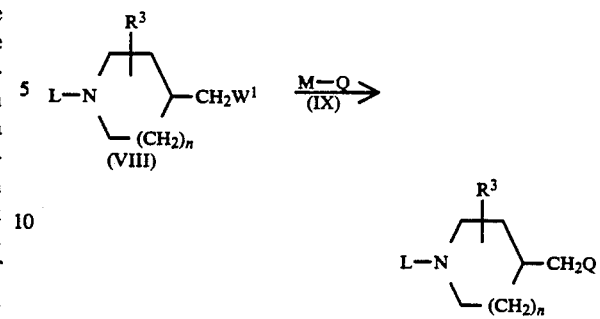

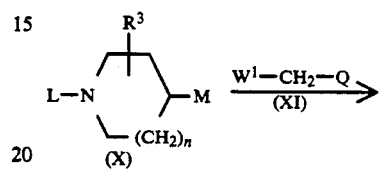

The reactions of (IV), (VI), (VIII) and (X) with respectively (V), (VII), (IX) and (XI) may conveniently be conducted in an appropriate reaction-inert solvent such as for example, an aromatic hydrocarbon, e.g., benzene, methylbenzene and the like; an ether, e.g. 1,4-dioxane, 1,1'-oxybisethane, tetrahydrofuran and the like; a halogenated hydrocarbon, e.g. trichloromethane and the like; N,N-dimethylformamide; N,N-dimethylacetamide; nitrobenzene; dimethylsulfoxide; 1-methyl-2-pyrrolidinone and the like; and when M is hydrogen, said solvent may also be a $C_{1-6}$alkanol, e.g., methanol, ethanol, 1-butanol and the like; a ketone, e.g., 2-propanone, 4-methyl-2-pentanone and the like. In some instances, particularly when B is a heteroatom, the addition of an appropriate base such as, for example, an alkali metal carbonate or hydrogen carbonate, e.g., sodium carbonate, sodium hydrogen carbonate and the like; sodium hydride; or an organic base such as, for example, N,N-diethylethanamine or N-(1-methylethyl)-2-propanamine and/or the addition of an iodide salt, preferably an alkali metal iodide, may be appropriate. Somewhat elevated temperatures and stirring may enhance the rate of the reaction.

The compounds of formula (I) wherein B is —$NR^4$—, said compounds being represented by formula (I-b), can also be prepared by reacting an intermediate of formula (XII) with an intermediate of formula (VII) wherein B-M represents a radical —$NR^4$—H, said intermediate being represented by formula (VII-a), following art-known reductive N-alkylation procedures.

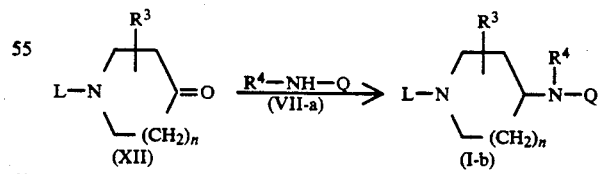

The reaction of (XII) with (VII-a) can conveniently be carried out by mixing the reactants in a suitable reaction-inert solvent with an appropriate reductant. Preferably, the ketone of formula (XII) is first reacted with the intermediate of formula (VII-a) to form an enamine, which optionally may be isolated and further purified, and subsequently reducing said enamine. Suitable solvents are, for example, water; $C_{1-6}$ alkanols, e.g., methanol, ethanol, 2-propanol and the like; ethers, e.g., 1,4-dioxane and the like; halogenated hydrocarbons, e.g., trichloromethane and the like; dipolar aprotic solvents, e.g., N,N-dimethylformamide, N,N-dimethylacetamide, dimethylsulfoxide and the like; or a mixture of such solvents. Appropriate reductants are for example, metal or complex metal hydrides, e.g., sodium borohydride, sodium cyanoborohydride, lithium aluminum hydride and the like. Alternatively, hydrogen in the presence of a suitable catalyst such as, for example, palladium-on-charcoal, platinum-on-charcoal and the like may be used as reductant. In order to prevent the undesired further hydrogenation of certain functional groups in the reactants and the reaction products it may be advantageous to add an appropriate catalyst poison to the reaction mixture such as, for example, thiophene and the like.

The compounds of formula (I-b) wherein B is —NH—, said compounds being represented by formula (I-b-1), can also be prepared by a cyclodesulfurization reaction of an appropriate thiourea of formula (II-a) wherein X is S, said thiourea being represented by formula (II-a-1), which may be formed in situ by condensing an isothiocyanate of formula (XIII) with a diamine of formula (III).

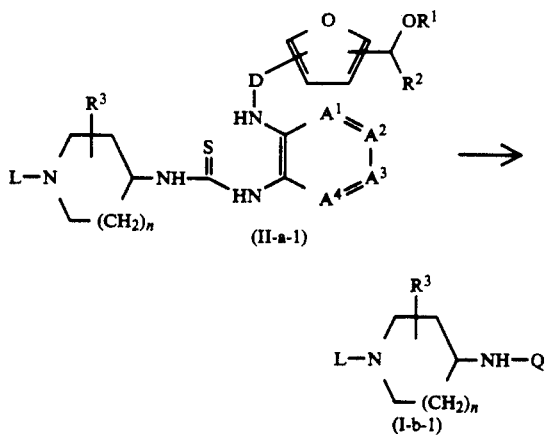

Said cyclodesulfurization reaction may be carried out by reacting (II-a-1) with an appropriate alkyl halide, preferably iodomethane, in a suitable reaction-inert organic solvent such as a $C_{1-6}$alkanol, e.g., methanol, ethanol, 2-propanol and the like. Alternatively, said cyclodesulfurization reaction may also be carried out by the reaction of (II-a-1) with an appropriate metal oxide or salt such as, for example, a Hg(II) or Pb(II) oxide or salt, e.g., HgO, HgCl$_2$, Hg(OAc)$_2$, PbO or Pb(OAc)$_2$ in an appropriate solvent following art-known procedures. In some instances it may be appropriate to supplement the reaction mixture with a small amount of sulfur. Also methanediimides, especially dicyclohexylcarbodiimide may be used as cyclodesulfurizing agents.

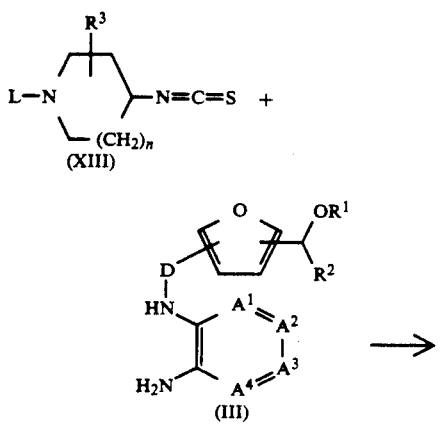

The compound of formula (I) can also be prepared by N-alkylating an intermediate of formula (XV) with an appropriate alkylating reagent of formula (XIV).

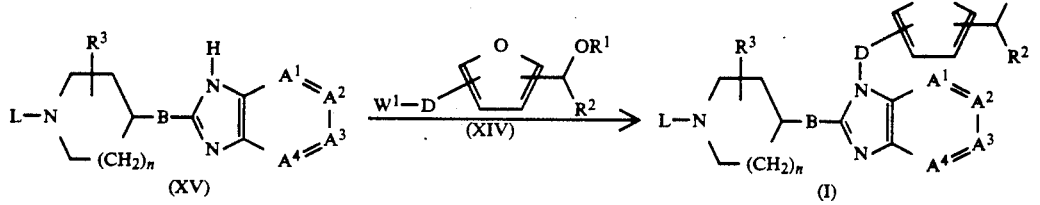

Said N-alkylation reaction can conveniently be conducted in a reaction-inert solvent such as, for example, water; an aromatic hydrocarbon, e.g., benzene, methylbenzene, dimethylbenzene and the like; an alkanol, e.g., methanol, ethanol, 1-butanol and the like; a ketone, e.g., 2-propanone, 4-methyl-2-pentanone and the like; an ether, e.g., tetrahydrofuran, 1,4-dioxane, 1,1'-oxybisethane and the like; a dipolar aprotic solvent, e.g., N,N-dimethylformamide, N,N-dimethylacetamide, dimethylsulfoxide, nitrobenzene, 1-methyl-2-pyrrolidinone and the like; or a mixture of such solvents. The addition of an appropriate base such as, for example, an alkali or an earth alkaline metal carbonate, hydrogen carbonate, alkoxide, hydride, amide, hydroxide or oxide, e.g., sodium carbonate, sodium hydrogen carbonate, potassium carbonate, sodium methoxide, sodium ethoxide, potassium tert.-butoxide, sodium hydride, sodium amide, sodium hydroxide, calcium carbonate, calcium hydroxide, calcium oxide and the like; or an organic base, such as, for example, a tertiary amine, e.g., N,N-diethylethanamine, N-(1-methylethyl)-2-propanamine, 4-ethylmorpholine, pyridine and the like may be utilized to pick up the acid which is liberated during the course of the reaction. In some instances the addition of an iodide salt, preferably an alkali metal iodide, is appropriate. Somewhat elevated temperatures and stirring may enhance the rate of the reaction. Additionally, it may be advantageous to conduct said N-alkylation under an inert atmosphere such as, for example, oxygen-free argon or nitrogen.

Alternatively, said N-alkylation may be carried out by applying art-known conditions of phase transfer catalysis reactions. Said conditions comprise stirring the reactants with an appropriate base and optionally under an inert atmosphere as described hereinabove, in the presence of a suitable phase transfer catalyst such sas, for example, a trialkylphenylmethylammonium, tetraalkylammonium, tetraalkylphosphonium, tetraarylphosphonium halide, hydroxide, hydrogen sulfate and the like catalysts.

The compounds of formula (I) wherein $R^1$ is hydrogen, said compounds being represented by formula (I-c), can also be prepared by condensing a furan derivative of formula (XVI) with an aldehyde $R^2$—CHO (XVII) in the presence of a suitable acid or base catalyst.

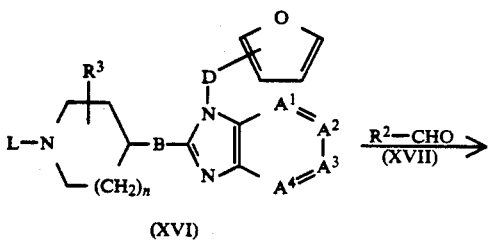

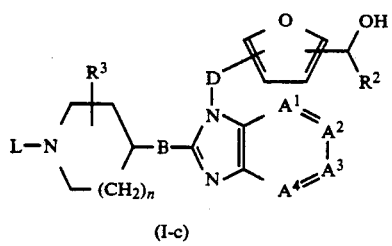

Said compounds of formula (I-c) can also be obtained by reducing a carboxylic acid derivative of formula (XVIII) wherein R is hydrogen, alkyl or aryl, with a reducing agent such as, for example, lithium aluminum hydride, lithium borohydride, sodium borohydride and the like in a reaction-inert solvent such as, for example, an ether, e.g. tetrahydrofuran, 1,1'-oxybisethane, 1,4-dioxane and the like; or alternatively, by reacting said carboxylic acid (XVIII) or a salt form thereof with an organometallic reagent, in particular $C_{1-6}$alkyl lithium, and reducing the thus obtained intermediate ketone with a reducing agent such as, for example, lithium aluminum hydride, lithium borohydride, sodium borohydride and the like in a reaction-inert solvent such as, for example, an ether, e.g. tetrahydrofuran, 1,1'-oxybisethane, 1,4-dioxane and the like.

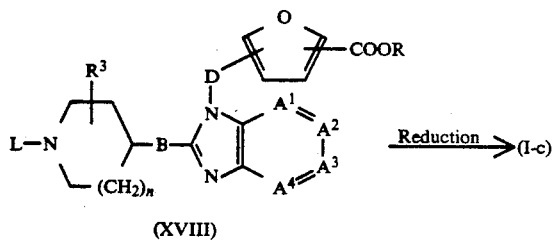

The compounds of formula (I) wherein L is other than hydrogen, said L being represented by $L^1$, and said compounds being represented by formula (I-d) can also be prepared by N-alkylating a compound of formula (I) wherein L is hydrogen, said compound being represented by (I-e), with an alkylating reagent of formula (XIX).

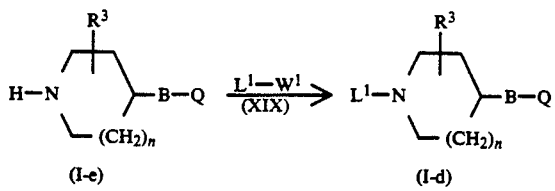

Said N-alkylation is conveniently conducted following art-known N-alkylation procedures as described hereinabove for the preparation of (I) from (XIV) and (XV).

The compounds of formula (I-d) wherein L is $C_{3-6}$cycloalkyl, $C_{1-12}$alkyl, a radical of formula (b-1), (b-2) or (b-3), said radicals being represented by the radical $L^2H$- and said compounds by formula (I-d-1) can also be prepared by the reductive N-alkylation reaction of (I-e) with an appropriate ketone or aldehyde of formula $L^2$=O (XX), said $L^2$=O being an intermediate of formula $L^2H_2$ wherein two geminal hydrogen atoms are replaced by =O, and $L^2$ is a geminal bivalent radical comprising $C_{3-6}$cycloalkylidene, $C_{1-12}$alkylidene, $R^5$—$C_{1-6}$alkylidene, $R^6$—Y—$C_{1-6}$alkylidene and $R^7$—$Z^2$—C(=X)—$Z^1$—$C_{1-6}$alkylidene.

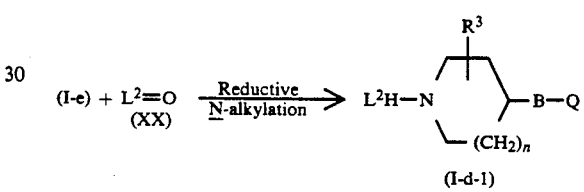

Said reductive N-alkylation can conveniently be carried out following the procedures described hereinabove for the preparation of compounds of formula (I-b) from (VII-a) and (XII), more particularly following the catalytic hydrogenation procedures.

The compounds of formula (I) wherein L is a radical of formula (b-2) and $R^6$ is aryl or Het, said $R^6$ being represented by $R^{6-a}$ and said compounds by formula (I-d-2) may also be prepared by alkylating a compound of formula (I) wherein L is a radical of formula (b-2) and $R^6$ is hydrogen, said compound being represented by formula (I-d-3), with a reagent of formula (XXI).

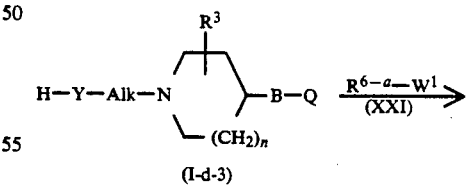

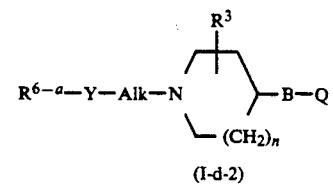

Similarly, the compounds of formula (I-d-2) may also be prepared by treating a compound of formula (I-d-4) with a reagent of formula (XXII).

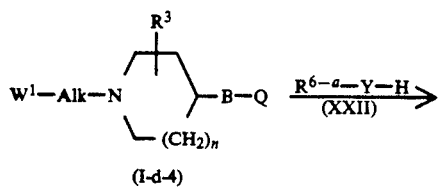

(I-d-4)

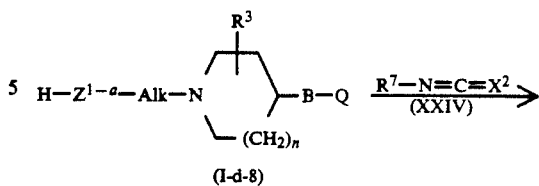

(I-d-8)

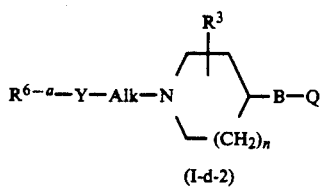

(I-d-2)

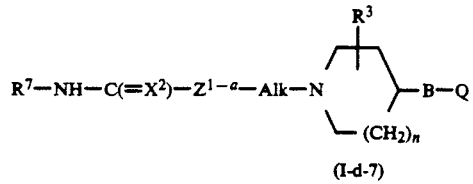

(I-d-7)

The alkylation reactions of (I-d-3) with (XXI) and (XXII) with (I-d-4) may conveniently be conducted in an inert organic solvent such as, for example, an aromatic hydrocarbon, e.g., benzene, methylbenzene, dimethylbenzene; a ketone, e.g., 2-propanone, 4-methyl-2-pentanone; an ether, e.g., 1,4-dioxane, 1,1'-oxybisethane, tetrahydrofuran; and a dipolar aprotic solvent, e.g., N,N-dimethylformamide; N,N-dimethylacetamide; dimethyl sulfoxide; nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. Somewhat elevated temperatures may enhance the rate of the reaction.

The compounds of formula (I) wherein L is a radical of formula (b-3), $Z^1$ is NH, $Z^2$ is other than a direct bond and X is other than $NR^{11}$, said $Z^2$ and X being represented by $Z^{2-a}$ and $X^2$, and said compounds by (I-d-5), can be prepared by reacting an isocyanate ($X^2$=O) or isothiocyanate ($X^2$=S) of formula (I-d-6) with a reagent of formula (XXIII).

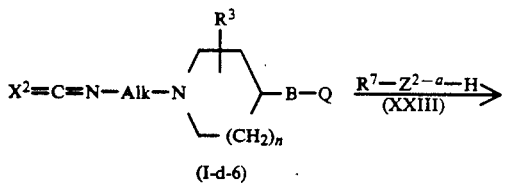

(I-d-6)

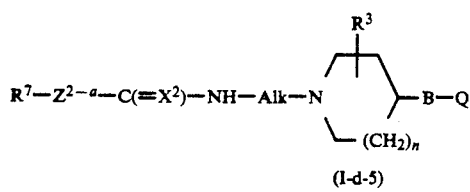

(I-d-5)

The compounds of formula (I) wherein L is a radical of formula (b-3), $Z^2$ is NH, $Z^1$ is other than a direct bond and X is other than $NR^{11}$, said $Z^1$ and X being represented by $Z^{1-a}$ and $X^2$, and said compounds by (I-d-7), can be prepared by reacting an isocyanate ($X^2$=O) or isothiocyanate ($X^2$=S) of formula (XXIV) with a compound of formula (I-d-8).

The reaction of (XXIII) with (I-d-6), or (XXIV) with (I-d-8) can generally be conducted in a suitable reaction-inert solvent such as, for example, an ether, e.g., tetrahydrofuran and the like, a halogenated hydrocarbon, e.g., trichloromethane and the like. Elevated temperatures may be suitable to enhance the rate of the reaction.

The compounds of formula (I) wherein L is a radical of formula (b-3), $Z^2$ is a direct bond, $Z^1$ is other than a direct bond and X is other than $NR^{11}$, said $Z^1$ and X being represented by $Z^{1-a}$ and $X^2$, said compounds being represented by (I-d-9), can be prepared by reacting a reagent of formula (XXV) or a reactive functional derivative thereof with a compound of formula (I-d-8).

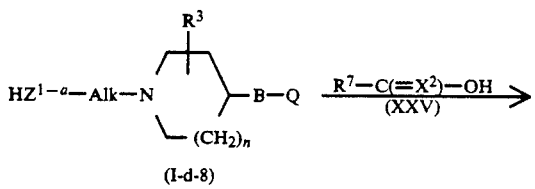

(I-d-8)

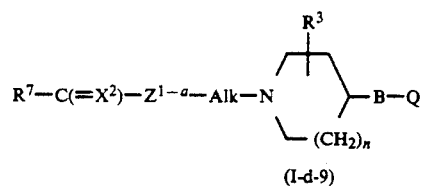

(I-d-9)

The reaction of (XXV) with (I-d-8) may generally be conducted following art-known esterification or amidation reaction procedures. For example, the carboxylic acid may be converted into a reactive derivative, e.g., an anhydride or a carboxylic acid halide, which subsequently is reacted with (I-d-8); or by reacting (XXV) and (I-d-8) with a suitable reagent capable of forming amides or esters, e.g., N,N-methanetetraylbis[cyclohexamine], 2-chloro-1-methylpyridinium iodide and the like. Said reactions may most conveniently be conducted in a suitable solvent such as, for example, an ether, e.g., tetrahydrofuran, a halogenated hydrocarbon, e.g., dichloromethane, trichloromethane, a dipolar aprotic solvent and the like. The addition of a base such as, for example, N,N-diethylethanamine and the like may be appropriate.

The compounds of formula (I) wherein L is a radical of formula $L^3$-$C_{2-6}$alkanediyl, said $L^3$ being aryl, Het, arylsulfonyl or a radical of formula $R^7$—$Z^2$—C(=X)—, and said compounds being represented by formula (I-d-

10), may also be prepared by the addition reaction of a compound of formula (I-e) to an appropriate alkene of formula (XXVI).

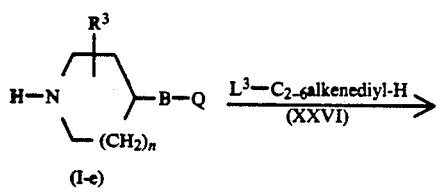

The compounds of formula (I) wherein L is 2-hydroxy-$C_{2-6}$alkyl or a radical of formula (b-4), said compounds being represented by formula (I-d-11), can be prepared by reacting a compound of formula (I-e) with an epoxide (XXVII) wherein $R^{14}$ is hydrogen, $C_{1-4}$alkyl or a radical $R^8$—O—$CH_2$—.

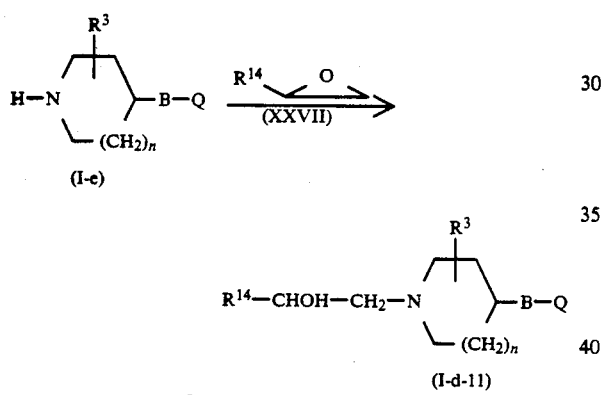

The reaction of (I-e) with respectively (XXVI) and (XXVII) may be conducted by stirring and, if desired, heating the reactants in a reaction-inert solvent such as, for example, a ketone, e.g., 2-propanone, 4-methyl-2-pentanone, an ether, e.g., tetrahydrofuran, 1,1'-oxybisethane, an alcohol, e.g., methanol, ethanol, 1-butanol, a dipolar aprotic solvent, e.g., N,N-dimethylformamide, N,N-dimethylacetamide, and the like.

The compounds of formula (I) wherein $R^5$, $R^6$ or $R^7$ are Het, may also be prepared following art-known procedures for preparing heterocyclic ring systems or following analogous methods. A number of such cyclization procedures are described in for example, U.S. Pat. No. 4,695,575 and in the references cited therein, in particular U.S. Pat. Nos. 4,335,127; 4,342,870 and 4,443,451, all incorporated herein by reference.

The compounds of formula (I) can also be converted into each other following art-known procedures of functional group transformation. Some examples of such procedures are cited hereinafter. The compounds of formula (I) containing a cyano substituent can be converted into the corresponding amines by stirring and, if desired, heating the starting cyano compounds in a hydrogen containing medium in the presence of an appropriate catalyst such as, for example, platinum-on-charcoal, Raney-nickel and the like catalysts. Suitable solvents are, for example, methanol, ethanol and the like. Amino groups may be converted into the corresponding isothiocyanato groups upon treatment with $CS_2$, optionally in the presence of N,N-methanetetraylbis[cyclohexamine]. Amino groups may be alkylated or acrylated following art-known procedures such as, for example, N-alkylation, N-acylation, reductive N-alkylation and the like methods. The compounds of formula (I) containing an amino group substituted with a radical aryl$CH_2$, may be hydrogenolyzed by treating the starting compound with hydrogen in the presence of a suitable catalyst, e.g., palladium-on-charcoal, platinum-on-charcoal and the like, preferably in an alcoholic medium.

In all of the foregoing and in the following preparations, the reaction products may be isolated from the reaction mixture and, if necessary, further purified according to methodologies generally known in the art.

Some intermediates and starting materials in the foregoing preparations are known compounds which may be prepared according to art-known methodologies of preparing said or similar compounds and others are new. A number of such preparation methods will be described hereinafter in more detail.

Starting materials such as the intermediates of formulae (II), (IV), (VI), (VIII), (X), (XII), (XIII), (XV) and (XVI) can conveniently be prepared following procedures similar to those described in for example, U.S. Pat. Nos. 4,219,559; 4,556,660; 4,634,704; 4,695,569; 4,695,575, 4,588,722, 4,835,161 and 4,897,401 and in EP-A-0,206,415; 0,282,133; 0,297,661 and 0,307,014.

The intermediates of formula (III) can be prepared from an aromatic starting material with vicinal halo and nitro substituents (XXVIII) by reaction with a suitable amine of formula (XXIX), followed by art-known nitro-to-amine reduction.

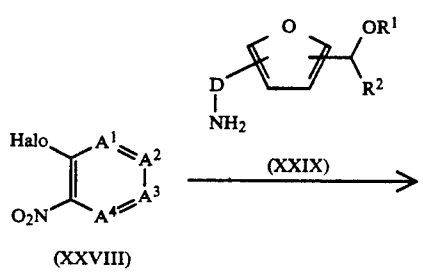

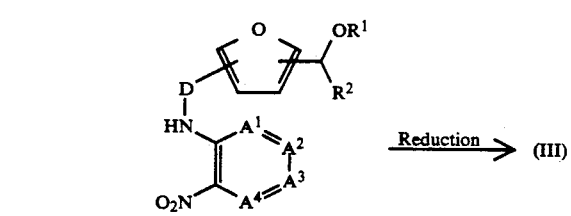

The intermediates of formulae (V), (VII), (IX) and (XI) then, can be prepared from the intermediates of formula (III) following art-known procedures of converting aromatic products with vicinal amino groups into benzimidazoles, imidazopyridines and/or purines.

The intermediates of formula (XVIII) can be conveniently prepared by N-alkylating an intermediate of formula (XV) with an appropriately substituted furancarboxylic acid derivative of formula (XXX) wherein R is hydrogen, alkyl or aryl, following the procedures described hereinabove for the preparation of the compounds of formula (I) from the intermediates (XV) and (XIV).

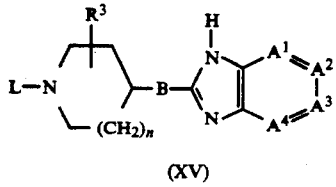 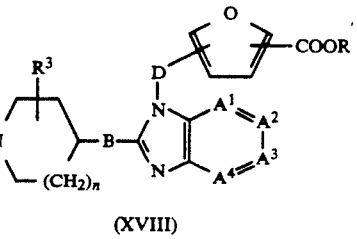

The compounds of formula (I), the pharmaceutically acceptable acid addition salts and stereochemically isomeric forms thereof possess useful pharmacological properties. More particularly, they are active antihistaminics which can clearly be demonstrated by, e.g., the results obtained in the test "Protection of Rats from Compound 48/80-induced lethality", the test "Histamine antagonism in Guinea Pig" and the test "Ascaris Allergy test in Dogs" described in Arch. Int. Pharmacodyn. Ther. 251, 39-51 (1981). Apart from their antihistaminic properties some of the the subject compounds generally also show serotonin-antagonism, as can be demonstrated in the test "Gastric Lesions induced by compount 48/80 in rats".

In view of their antihistaminic and serotoninergic properties, the compounds of formula (I) and their acid addition salts are very useful in the treatment of allergic diseases such as for example, allergic rhinitis, allergic conjunctives, chronic urticaria, allergic asthma and the like.

In view of their useful antiallergic properties the subject compounds may be formulated into various pharmaceutical forms for administration purposes. To prepare the antiallergic compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the composition in oral dosage form, any of the usual pharmaceutical media may be employed such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on or as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention also relates to a method of treating warm-blooded animals suffering from said allergic diseases by administering to said warm-blooded animals an antiallergically effective amount of a compound of formula (I) or a pharmaceutically acceptable acid addition salt form thereof.

Those of skill in treating allergic diseases in warm-blooded animals could easily determine the effective amount from the test results presented hereinafter. In general it is contemplated that an antiallergically effective amount would be from about 0.001 mg/kg to about 100 mg/kg body weight, and more preferably from about 0.01 mg/kg to about 1 mg/kg body weight.

The following examples are intended to illustrate and not to limit the scope of the present invention in all its aspects. Unless otherwise stated all parts therein are by weight.

EXPERIMENTAL PART

A. PREPARATION OF THE INTERMEDIATES

EXAMPLE 1

A mixture of 28.8 parts of ethyl 4-(1H-benzimidazol-2-ylamino)-1-piperidinecarboxylate (as prepared in Example XIV of U.S. Pat. No. 4,219,559), 33.9 parts of ethyl 5-chloromethyl-2-furancarboxylate, 15.9 parts of sodium carbonate and 282 parts of N,N-dimethylformamide was stirred for 2 nights at 70° C. The reaction mixture was poured into water and the product was extracted with methylbenzene. The extract was washed with water, dried, filtered and evaporated. The residue was purified by column chromatography (silica gel; CHCl$_3$/CH$_3$OH 97:3). The eluent of the desired fraction was evaporated and the residue was stirred in 1,1'-oxybisethane. The precipitate was filtered off and dried, yielding 31.2 parts (70.8%) of ethyl 4-[[1-[[5-(ethoxycarbonyl)-2-furanyl]-methyl]-1H-benzimidazol-2-yl]amino]-1-piperidinecarboxylate; mp. 136.0° C. (interm. 1).

In a similar manner ethyl 4-(1H-benzimidazol-2-ylamino)hexahydro-1H-azepine-1-carboxylate (as prepared in Example 9 of EP-0,297,661, published Jan. 4, 1989) was converted into ethyl 4-[[1-[[5-(ethoxycarbonyl)-2-furanyl]methyl]-1H-benzimidazol-2-yl]amino]-hexahydro-1H-azepine-1-carboxylate (interm. 2) and ethyl 3-(1H-benzimidazol-2-ylamino)-1-pyrrolidinecarboxylate monohydrochloride (as prepared in Example 8 of EP-0,297,661, published Jan. 4, 1989) into ethyl 3-[[1-[[5-(ethoxycarbonyl)-2-furanyl]methyl]-1H-benzimidazol-2-yl]amino]-1-pyrrolidinecarboxylate (interm. 3).

EXAMPLE 2

To 470 parts of N,N-dimethylformamide were added portionwise 17.3 parts of a dispersion of sodium hydride in mineral oil (50%) and 91.6 parts of 2-[[1-(phenylmethyl)-4-piperidinyl]methyl]-1H-benzimidazole (as prepared in Example 16 of U.S. Pat. No. 4,695,575) while stirring under a nitrogen atmosphere. After stirring for 1 hour, 67.9 parts of ethyl 5-chloromethyl-2-furancarboxylate were added dropwise while cooling. Stirring was continued for 1 hour and then water was added to the reaction mixture. The product was extracted with methylbenzene and the extract was washed with water, dried, filtered and evaporated. The residue was dried azeotropically with methylbenzene (2x), yielding 119 parts (86.7%) of ethyl 5-[[2-[[1-(phenylmethyl)-4-piperidinyl]methyl]-1H-benzimidazol-1-yl]methyl]-2-furancarboxylate (interm. 4). Following the same procedure and starting from the appropriate starting materials, there were also prepared:
methyl 5-[[2-[[1-[2-(4-methoxyphenyl)ethyl]-4-piperidinyl]amino]-1H-benzimidazol-1-yl]methyl]-2-furancarboxylate; mp. 124.4° C. (interm. 5),
ethyl 5-[[2-[[1-[2-(4-methoxyphenyl)ethyl]-4-piperidinyl]amino]-1H-benzimidazol-1-yl]methyl]-3-furancarboxylate; mp. 121.9° C. (interm. 6),
methyl 5-[[2-[(1-methyl-4-piperidinyl)amino]-1H-benzimidazol-1-yl]methyl]-2-furancarboxylate; mp. 169.5° C. (interm. 7),
ethyl 5-[[2-[(1-methyl-4-piperidinyl)amino]-1H-benzimidazol-1-yl]methyl]-3-furancarboxylate (E)-2-butenedioate(1:2); mp. 200.9° C. (interm. 8),
ethyl 2-[[2-[[1-[2-(4-methoxyphenyl)ethyl]-4-piperidinyl]amino]-1H-benzimidazol-1-yl]methyl]-3-furancarboxylate (interm. 9),
ethyl 4-[[1-[[3-(ethoxycarbonyl)-2-furanyl]methyl]-1H-benzimidazol-2-yl]amino]-1-piperidinecarboxylate; mp. 162.3° C. (interm. 10), ethyl 4-[[1-[[2-(methoxycarbonyl)-3-furanyl]methyl]-1H-benzimidazol-2-yl]amino]-1-piperidinecarboxylate (interm. 11), and
methyl 3-[[2-[[1-[2-(4-methoxyphenyl)ethyl]-4-piperidinyl]amino]-1H-benzimidazol-1-yl]methyl]-2-furancarboxylate (interm. 12).

EXAMPLE 3 a) A mixture of 55 parts of N-(2-furanylmethyl)-3-nitro-2-pyridinamine, 2 parts of a solution of thiophene in methanol (4%) and 400 parts of methanol saturated with ammonia was hydrogenated at normal pressure and at room temperature with 4 parts of a platinum-on-charcoal catalyst 5%. After the calculated amount of hydrogen was taken up, the catalyst was filtered off and the filtrate was evaporated, yielding 48 parts of N$^2$-(2-furanylmethyl)-2,3-pyridinediamine as a residue (interm. 13).

b) A mixture of 54 parts of ethyl 4-isothiocyanato-1-piperidinecarboxylate, 48 parts of intermediate (13) and 450 parts of tetrahydrofuran was stirred overnight at reflux temperature. The reaction mixture was evaporated and the residue was crystallized from a mixture of 2-propanone and 2,2'-oxybispropane, yielding 76 parts (75%) of ethyl 4-[[[2-[(2-furanylmethyl)amino]-3-pyridinyl]aminothioxomethyl]amino]-1-piperidinecarboxylate; mp. 132.7° C. (interm. 14). In a similar manner ethyl hexahydro-4-isothiocyanato-1H-azepine-1-carboxylate (as prepared in Example 9 of EP-0,297,661, published Jan. 4, 1989) was converted into ethyl hexahydro-4-[[[[2-[[[5-(hydroxymethyl)-2-furanyl]methyl]amino]-3-pyridinyl]amino]thioxomethyl]amino]-1H-azepine-1-carboxylate (interm. 15).

c) A mixture of 74 parts of intermediate (14), 96 parts of mercury(II)oxide, 0.1 parts of sulfur and 800 parts of ethanol was stirred and refluxed for 3 hours. The reaction mixture was filtered over diatomaceous earth and the filtrate was evaporated. The residue was crystallized from acetonitrile, yielding 52.5 parts (79%) of ethyl 4-[[3-(2-furanylmethyl)-3H-imidazo[4,5-b]pyridin-2-yl]amino]-1-piperidinecarboxylate; mp. 149.2° C. (interm. 16).

EXAMPLE 4 a) A mixture of 16.3 parts of 4,6-dichloro-5-pyrimidinamine, 14 parts of 5-(aminomethyl)-2-furanmethanol, 12 parts of N,N-diethylethanamine and 200 parts of water was stirred for 10 hours at reflux temperature. The reaction mixture was evaporated and the residue was purified by column chromatography (silica gel; CH$_2$Cl$_2$/CH$_3$OH(NH$_3$) 95:5). The eluent of the desired fraction was evaporated and the residue was crystallized from acetonitrile. The product was filtered off and dried, yielding 19.5 parts (76.6%) of 5-[[(5-amino-6-chloro-4-pyrimidinyl)amino]methyl]-2-furanmethanol; mp. 136.7° C. (interm. 17).

b) A mixture of 18.5 parts of intermediate (17), 1 part of a solution of thiophene in methanol 4%, 119 parts of methanol and 10 parts of calciumoxide was hydrogenated at normal pressure and room temperature with 4 parts of palladium-on-charcoal catalyst 10%. After the calculated amount of hydrogen was taken up, the catalyst was filtered off and the filtrate was evaporated, yielding 15.9 parts (100%) of 5-[[(5-amino-4-pyrimidinyl)amino]methyl]-2-furanmethanol (interm. 18).

EXAMPLE 5 a) A mixture of 15.9 parts of 4-chloro-3-nitropyridine, 12.7 parts of 5-(aminomethyl)-2-furanmethanol, 13.3 parts of N,N-diethylethanamine and 745 parts of trichloromethane was stirred for 3 hours at reflux temperature. After cooling, the reaction mixture was washed with K$_2$CO$_3$ (aq.), dried, filtered and evaporated. The residue was crystallized from acetonitrile. The product was filtered off and dried, yielding 17.76 parts (71.3%) of 5-[[(3-nitro-4-pyridinyl)amino]methyl]-2-furanmethanol; mp. 134.9° C. (interm. 19).

b) A mixture of 17.3 parts of intermediate (19), 1 part of a solution of thiophene in methanol 4% and 158 parts of methanol was hydrogenated at normal pressure and room temperature with 1 part of platinum-on-charcoal catalyst 5%. After the calculated amount of hydrogen was taken up, the catalyst was filtered off and the filtrate was evaporated. The residue was crystallized from acetonitrile. The product was filtered off and dried, yielding 12.7 parts (83.9%) of 5-[[(3-amino-4-pyridinyl)amino]methyl]-2-furanmethanol (interm. 20).

c) A mixture of 14.3 parts of ethyl 4-isothiocyanato-1-piperidinecarboxylate, 12.7 parts of intermediate (20) and 188 parts of N,N-dimethylformamide was stirred overnight at 60° C. The reaction mixture was evaporated, yielding 25.1 parts (100%) of ethyl 4-[[[[4-[[[5-(hydroxymethyl)-2-furanyl]methyl]amino]-3-pyridinyl]-amino]thioxomethyl]amino]-1-piperidinecarboxylate (interm. 21). Following the same procedure, intermediate (18) was converted into ethyl 4-[[[[4-[[[5-(hydroxymethyl)-2-furanyl]methyl]amino]-5-pyrimidinyl]-amino]thioxomethyl]amino]1-piperidinecarboxylate (interm. 22).

EXAMPLE 6 a) To a solution of 25 parts of 1-(phenylmethyl)-4-piperidineacetonitrile in 178 parts of tetrahydrofuran were added dropwise 37.97 parts of ethyl chloroformate at room temperature. The reaction mixture was stirred for 15 hours at room temperature and was then evaporated. The residue was taken up in 90 parts of ethyl acetate and the whole was washed successively with HCl 3N, NaHCO$_3$ and NaCl (sat.). The solvent was evaporated and the residue was distilled (100°-110° C./6.7 Pa), yielding 18.7 parts (81.4%) of ethyl 4-(cyanomethyl)-1-piperidinecarboxylate (interm. 24).

b) A mixture of 18,32 parts of intermediate (24), 4.30 parts of ethanol and 74.5 parts of trichloromethane was cooled in an ice-bath while hydrochloric acid was bubbled through for 30 minutes. The reaction mixture was left in a refrigerator for 48 hours and was then evaporated. The residue was triturated with 142 parts of 1,1'-oxybisethane. The product was dried in vacuo, yielding 14.2 parts (54.1%) of ethyl 4-(2-ethoxy-2-iminoethyl)-1-piperidinecarboxylate monohydrochloride (interm. 25). Following the same procedure, 1-(phenylmethyl)-4-piperidineacetonitrile was converted into O-ethyl 1-(phenylmethyl)-4-piperidineethanimidate dihydrochloride (interm. 26).

B. PREPARATION OF THE FINAL COMPOUNDS

EXAMPLE 7 a) To a stirred mixture of 4.4 parts of intermediate (1) and 133.5 parts of tetrahydrofuran were added dropwise 5 ml. of a solution of lithium tetrahydroborate in tetrahydrofuran 2M under a nitrogen atmosphere. Stirring was continued overnight at reflux temperature and then there were added successively 2-propanone and acetic acid. The whole was evaporated. The residue was taken up in water and basified with K$_2$CO$_3$. The product was extracted with dichloromethane. The extract was dried, filtered and evaporated. The residue was crystallized from 4-methyl-2-pentanone, yielding 2.08 parts (52.2%) of ethyl 4-[[1-[[5-hydroxymethyl)2-furnanyl]methyl]-1H-benzimi-dazol-2-yl]amino]-1-piperidinecarboxylate; mp. 141.6° C. (comp. 3.05).

b) A mixture of 75.7 parts of compound (3.05), 106.5 parts of potassium hydroxide and 390 parts of 2-propanol was stirred overnight at reflux temperature. After cooling, the reaction mixture was evaporated and the residue was taken up in water. The product was extracted with dichloromethane and the extract was filtered over diatomaceous earth. The filtrate was evaporated and the residue was crystallized from 2-propanone, yielding 46.5 parts (75.0%) of 5-[[2-(4-piperidinylamino)-1H-benzimidazol-1-yl]methyl]-2-furanamethanol; mp. 156.3° C. (comp. 3.11).

c) A mixture of 4.53 parts of chloroacetonitrile, 16.26 parts of compound (3.11), 8 parts of sodium carbonate and 141 parts of N,N-dimethylformamide was stirred for 2 hours at room temperature. The reaction mixture was poured into water and the product was extracted with trichloromethane. The extract was dried, filtered and evaporated. The residue was stirred in 2,2'-oxybispropane and the product was filtered off, yielding 17.71 parts (96.9%) of 4-[[1-[[5-(hydroxymethyl)-2-furanyl]-methyl]-1H-benzimidazol-2-yl]amino]-1-piperidineacetonitrile; mp. 209.8° C. (comp. 3.22).

d) A mixture of 16.6 parts of compound (3.22) and 790 parts of methanol saturated with ammonia was hydrogenated at normal pressure and at room temperature with 6 parts of Raney nickel. After the calculated amount of hydrogen was taken up, the catalyst was filtered off and the filtrate was evaporated. The residue was crystallized successively from acetonitrile and 2-propanol, yielding 7.4 parts (43.5%) of 5-[[2-[[1-(2-aminoethyl)-4-piperidinyl]amino]-1H-benzimidazol-1-yl]methyl]-2-furanmethanol; mp. 164.6° C. (comp. 3.23).

e) To a stirred solution of 1.38 parts of 1-methyl-1H-2-pyrrolecarboxylic acid, 2.81 parts of 2-chloro-1-methylpyridinium iodide, 2.2 parts of N,N-diethylethanamine and 199.5 parts of dichloromethane was added a solution of 3.7 parts of compound (3.23) in a mixture of dichloromethane and N,N-dimethylacetamide. After stirring for 3 hours, the reaction mixture was poured into water. The product was extracted with dichloromethane and the extract was dried, filtered and evaporated. The residue was purified by column chromatography (silica gel; CHCl$_3$/CH$_3$OH (NH$_3$) 95:5). The eluent of the desired fraction was evaporated and the residue was crystallized from acetonitrile, yielding 2.25 parts (47.2%) of N-[2-[4-[[1-[[5-(hydroxymethyl)-2-furanyl]methyl]-1H-benzimidazol-2-yl]amino]-1-piperidinyl]-ethyl]-1-methyl-1H-pyrrole-2-carboxamide; mp. 182.2° C. (comp. 3.24).

EXAMPLE 8 a) To a stirred and refluxing mixture of 12 parts of lithium aluminum hydride in 445 parts of tetrahydrofuran, was added dropwise a solution of 137 parts of intermediate (4) in tetrahydrofuran under a nitrogen atmosphere. Refluxing was continued for 1 hour. After cooling, there were added successively ethyl acetate, 42 parts of NaOH 15% (dropwise) and 36 parts of water. The whole was stirred and filtered. The filtrate was evaporated and the residue was taken up in water. The product was extracted with dichloromethane and the extract was dried, filtered and evaporated. The residue was crystallized from acetonitrile, yielding 64.1 parts (51.4%) of 5-[[2-[[1-(phenylmethyl)-4-piperidinyl]methyl]-1H-benzimidazol-1-yl]methyl]-2-furanmethanol; mp. 143.8° C. (comp. 1.01).

b) To a stirred mixture of 14.1 parts of 2-chloro-1-methylpyridinium iodide, 11.5 parts of N,N-diethylethanamine and 282 parts of N,N-dimethylformamide were added dropwise 3.3 parts of acetic acid at room temperature. After stirring for 1 hour, 41.5 parts of compound (1.01) were added. Stirring was continued overnight and then the reaction mixture was poured into water. The product was extracted with dichloromethane and the extract was dried, filtered and evaporated, yielding 40 parts (87.4%) of 5-[[2-[[1-(phenylmethyl)-4-piperidinyl]methyl]-1H-benzimidazol-1-yl]methyl]-2-furanmethanol acetate (ester) (comp. 1.02).

c) To a stirred and refluxing mixture of 45.8 parts of compound (1.02) and 261 parts of methylbenzene, were added dropwise 12 parts of ethyl chloroformate. Refluxing was continued for 1 hour. After cooling, water was added to the reaction mixture and the product was extracted with methylbenzene. The extract was dried, filtered and evaporated, yielding 44.0 parts (100%) of ethyl 4-[[1-[[5-[(acetyloxy)-methyl]-2-furanyl]methyl]-1H-benzimidazol-2-yl]methyl]-1-piperidinecarboxylate (comp. 1.03). This compound also contained an amount of a side product, namely ethyl 4-[[1-[[5-[[(phenyl)methoxy]methyl]-2-furanyl]methyl]-1H-benzimidazol-2-yl]methyl]-1-piperidinecarboxylate.

d) A mixture of 44.0 parts of compound (1.03), 56 parts of potassium hydroxide and 234 parts of 2-propanol was stirred overnight at reflux temperature. The reaction mixture was evaporated and the residue was taken up in water. The product was extracted with dichloromethane and the extract was dried, filtered and evaporated. The residue was purified by column chromatography (silica gel; $CHCl_3/CH_3OH$ ($NH_3$) 95:5→80:20). The eluent of the second fraction was evaporated, yielding 27.5 parts (84.5%) of 5-[[2-(4-piperidinylmethyl)-1H-benzimidazol-1-yl]methyl]-2-furanmethanol (comp. 1.04).

Evaporation of the first fraction yielded 9 parts of 2-[[5-(phenylmethoxy)methyl]-2-furanyl]methyl]-2-(4-piperidinylmethyl)-1H-benzimidazole (comp. 1.05).

e) A mixture of 3.25 parts of compound (1.04), 2 parts of polyoxymethylene, 2 parts of a solution of thiophene in methanol 4% and 119 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was taken up in dichloromethane and the whole was washed with $NH_4OH$ (aq.). The organic layer was dried, filtered and evaporated. The residue was crystallized successively from 4-methyl-2-pentanone and acetonitrile, yielding 1.72 parts (50.7%) of 5-[[2-[(1-methyl-4-piperidinyl)methyl]-1H-benzimidazol-1-yl]methyl]-2-furanmethanol; mp. 158.1° C. (comp. 1.17).

EXAMPLE 9

Through a stirred mixture of 8.4 parts of intermediate (16), 5.05 parts of a formaldehyde solution 40% and 4.25 parts of piperidine was bubbled hydrochloric acid till all solid entered the solution. The whole was stirred over weekend and treated with ammonia. The product was extracted with trichloromethane. The extract was dried, filtered and evaporated. The residue was purified by column chromatography (silica gel; $CHCl_3/CH_3OH$ 97:3→98:2). The eluent of the desired fractions was evaporated and the residue was crystallized from a mixture of 4-methyl-2-pentanone and 2,2'-oxybispropane, yielding 1.0 part (12.5%) of ethyl 4-[[3-[[5-(hydroxymethyl)-2-furanyl]-methyl]-3H-imidazo[4,5-b]pyridin-2-yl]amino]-1-piperidinecarboxylate; mp. 148.3° C. (comp. 2.01).

EXAMPLE 10

A mixture of 105.9 parts of intermediate (25), 197.5 parts of 5-[[(3-amino-2-pyridinyl)amino]methyl]-2-furanmethanol and 470 parts of N,N-dimethylformamide was stirred for 3 days at room temperature. The reaction mixture was poured into water. The whole was basified with $K_2CO_3$ and extracted with dichloromethane. The extract was dried, filtered and evaporated and the residue was taken up in 435 parts of methylbenzene. A few parts of 4-methylbenzenesulfonic acid were added and the whole was stirred for 2 hours at reflux temperature. After cooling and basifying with $K_2CO_3$ (aq.), the product was extracted with dichloromethane and the extract was dried, filtered and evaporated, yielding 156 parts (100%) of ethyl 4-[[3-[[5-(hydroxymethyl)-2-furanyl]methyl]-3H-imidazo]4,5-b]pyridin-2-yl]methyl]-1-piperidinecarboxylate (comp. 2.13).

EXAMPLE 11

A mixture of 20 parts of compound (3.05) and 237 parts of methanol was acidified with sulfuric acid (pH 1) while stirring. Stirring was continued overnight at reflux temperature. After cooling, the reaction mixture was basified with methanol saturated with ammonia and was then evaporated. The residue was taken up in water and the product was extracted with dichloromethane. The extract was dried, filtered and evaporated. The residue was purified by column chromatography (silica gel; $CHCl_3/CH_3OH$ 97:3). The eluent of the desired fraction was evaporated, yielding 29 parts (100%) of ethyl 4-[[1-[[5-(methoxymethyl)-2-furanyl]methyl]-1H-benzimidazol-2-yl]amino]-1-piperidinecarboxylate (comp. 3.06).

EXAMPLE 12

A mixture of 2 parts of [(4-fluorophenoxy)methyl]oxirane, 3.26 parts of compound (3.11) and 39 parts of 2-propanol was stirred for 48 hours at reflux temperature. The reaction mixture was evaporated and the residue was purified by column chromatography (silica gel; $CHCl_3/CH_3OH$ ($NH_3$) 97:3). The eluent of the desired fraction was evaporated and the residue was crystallized from a mixture of acetonitrile and 2,2'-oxybispropane, yielding 2.80 parts (56.6%) of α-[(4-fluorophenoxy)methyl]-4-[[1-[[5-(hydroxymethyl)-2-furanyl]methyl]-1H-benzimidazol-2-yl]amino]-1-piperidineethanol; mp. 136.8° C. (comp. 3.20).

EXAMPLE 13

To a stirred and cooled (0° C.) mixture of 3.3 parts of compound (3.11), 1.01 parts of 1,1'-oxybisethane and 94 parts of N,N-dimethylformamide was added dropwise a solution of 0.8 parts of acetylchloride in N,N-dimethylformamide. The reaction mixture was allowed to warm up to room temperature and was then evaporated. The residue was boiled 4 times in trichloromethane and decanted. The combined liquid phases were dried, filtered and evaporated. The residue was purified by column chromatography (silica gel; $CH_2Cl_2/CH_3OH$ 95:5). The eluent of the desired fraction was evaporated and the residue was crystallized from methanol, yielding 0.8 parts (21.7%) of 1-acetyl-N-[1-[[5-(hydroxymethyl)-2-furanyl]methyl]-1H-benzimidazol-2-yl]4-piperidinamine; mp. 213.9° C. (comp. 3.21).

EXAMPLE 14

A mixture of 3.7 parts of 7-(2-bromoethyl)-3,4-dihydro-8-methyl-2-H,6H-pyrimido[2,1-b][1,3]thiazin-6-one monohydrobromide, 3.2 parts of compound (3.11), 2.1 parts of sodium carbonate and 160 parts of 4-methyl-2-pentanone was stirred overnight at reflux temperature. The reaction mixture was evaporated and the residue was taken up in water. The product was extracted with dichloromethane and the extract was dried, filtered and evaporated. The residue was purified by column chromatography (silica gel; $CH_2Cl_2/CH_3OH(NH_3)$ 95:5). The eluent of the desired fraction was evaporated and the residue was crystallized from acetonitrile. The product was filtered off and dried, yielding 1.5 parts (28.0%) of 3,4-dihydro-7-[2-[4-[[1-[[5-(hydroxymethyl)-2-furanyl]methyl]-1H-benzimidazol-2-yl]amino]-1-piperidinyl]ethyl]-8-methyl-2H,6H-pyrimido[2,1-b][1,3[thiazin-6-one; mp. 226.9° C. (comp. 3.31).

EXAMPLE 15

A mixture of 3.3 parts of 2-chloroacetonitrile, 13 parts of compound (2.03), 5 parts of N,N-diethylethanamine and 94 parts of N,N-dimethylformamide was stirred for 4 hours at room temperature. After the addition of potassium carbonate, the reaction mixture was diluted with water. The whole was stirred briefly and the product was extracted with dichloromethane. The extract was dried, filtered and evaporated. The residue was stirred in 1,1'-oxybisethane, filtered off and dried, yielding 10.85 parts (74%) of 4-[[3-[[5-(hydroxymethyl)-2-furanyl]methyl]-3H-imidazo[4,5-b]pyridin-2-yl]amino]-1-piperidineacetonitrile (comp. 2.26).

EXAMPLE 16

A mixture of 3 parts of 2-ethenylpyridine, 3.7 parts of compound (2.28) and 122 parts of 1-butanol was stirred overnight at reflux temperature. The reaction mixture was evaporated and the residue was purified by column chromatography (silica gel; $CH_2Cl_2/CH_3OH(NH_3)$ 90:10:0→90:8:2). The eluent of the desired fraction was evaporated and the residue was converted into the (E)-2-butenedioate (2:3) salt in ethanol. The salt was recrystallized from ethanol (2x), yielding 2.14 parts (35.3%) of 5-[[2-[[1-[2-(2-pyridinyl)ethyl]-4-piperidinyl]methyl]-3H-imidazo[4,5-b]-pyridin-3-yl]methyl]-2-furanmethanol (E)-2-butenedioate(2:3); mp. 159.8° C. (comp. 2.35).

EXAMPLE 17

A mixture of 4.5 parts of 3,6-dichloropyridazine, 11.1 parts of compound (1.14) and 3.2 parts of sodium carbonate was stirred for ½ hour at 150° C. After cooling, the reaction mixture was diluted with water. The product was extracted with trichloromethane and the extract was dried, filtered and evaporated. The residue was boiled in acetonitrile. After cooling, the precipitate was filtered off and dried, yielding 9.72 parts (67.4%) of 5-[[2-[[1-[2-[(6-chloro-3-pyridazinyl)amino]ethyl]-4-piperidinyl]-methyl]-1H-benzimidazol-1-yl]methyl]-2-furanmethanol; mp. 188.4° C. (comp. 1.21).

EXAMPLE 18

A mixture of 1.1 parts of 4-chloro-3-nitropyridine, 2.5 parts of compound (3.23), 1 part of sodium carbonate and 39.5 parts of ethanol was stirred overnight at room temperature. Water was added and the product was extracted with dichloromethane. The extract was dried, filtered and evaporated. The residue was crystallized from a mixture of acetonitrile and ethanol, yielding 1.9 parts (56.8%) of 5-[[2-[[1-[2-[(3-nitro-4-pyridinyl)amino]-ethyl]-4-piperidinyl]amino]-1H-benzimidazol-1-yl]methyl]-2-furanmethanol; mp. 191.0° C. (comp. 3.26).

EXAMPLE 19

A mixture of 1.74 parts of 4-chloro-3-nitropyridine, 4.22 parts of compound (4.11), 1.11 parts of N,N-diethylethanamine and 149 parts of trichloromethane was stirred overnight at room temperature. The reaction mixture was washed with $K_2CO_3$ (aq.). The aqueous layer was separated and extracted with dichloromethane. The combined organic layers were dried, filtered and evaporated. The residue was purified by column chromatography (silica gel; $CH_2Cl_2/CH_3OH/C-H_3OH(NH_3)$ 90:10:1). The eluent of the desired fraction was evaporated and the residue was crystallized from a mixture of 4-methyl-2-pentanone and ethanol. The product was filtered off and dried, yielding 1.2 parts (21.2%) of 5-[[2-[[hexahydro-1-[2-[(3-nitro-4-pyridinyl)amino]ethyl]-1H-azepin-4-yl]amino]-1H-benzimidazol-1-yl]methyl]-2-furanmethanol hemihydrate; mp. 155.1° C. (comp. 4.14).

EXAMPLE 20

To a solution of 1.3 parts of lithium aluminum hydride in 89 parts of tetrahydrofuran was added a solution of 4.6 parts of intermediate (3) in tetrahydrofuran. After refluxing for 2 hours, the reaction mixture was treated with ethyl acetate. Then there were added dropwise 7.9 parts of NaOH 15% and 4.8 parts of water, while stirring. The whole was filtered over diatomaceous earth and the filtrate was evaporated. The residue was purified by column chromatography (silica gel; $CH_2Cl_2/CH_3OH/CH_3OH$ ($NH_3$) 90:5:5). The eluent of the desired fraction was evaporated and the residue was crystallized from a mixture of acetonitrile and 2,2'-oxybispropane (2x), yielding 0.65 parts (18.4%) of 5-[[2-[(hexahydro-1-methyl-1H-azepin-4-yl)amino]-1H-benzimidazol-1-yl]methyl]-2-furanmethanol (comp. 4.02).

EXAMPLE 21

A mixture of 2.5 parts of 3-bromo-N-(1-methylethyl)-propanamide, 3.26 parts of compound (3.11), 1.26 parts of sodium hydrogen carbonate and 39.5 parts of ethanol was stirred overnight at reflux temperature. The reaction mixture was evaporated and the residue was taken up in water. The product was extracted with a mixture of trichloromethane and ethanol and the extract was dried, filtered and evaporated. The residue was crystallized from acetonitrile, yielding 3.20 parts (72.8%) of 4-[[1-[[5-(hydroxymethyl)-2-furanyl[methyl[-1H-benzimidazol-2-yl]amino]-N-(1-methylethyl)-1-piperidinepropanamide; mp. 139.7° C. (comp. 3.12).

EXAMPLE 22

A mixture of 4.36 parts of compound (1.21), 1 part of a solution of thiophene in methanol 4%, 198 parts of methanol and 2 parts of calciumoxide was hydrogenated at normal pressure and room temperature with 2 parts of palladium-on-charcoal catalyst 10%. After the calculated amount of hydrogen was taken up, the catalyst was filtered off and the filtrate was evaporated. The residue was taken up in water and the product was extracted with dichloromethane. The extract was dried, filtered and evaporated. The residue was purified by column chromatography (silica gel; CH₂Cl₂/CH₃OH(NH₃) 95:5). The eluent of the desired fraction was evaporated and the residue was converted into the ethanedioate (1:3) salt in a mixture of methanol and ethanol. The product was filtered off and dried, yielding 4.51 parts (69.9%) of 5-[[2-[[1-[2-(3-pyridazinylamino)ethyl]-4-piperidinyl]methyl]-1H-benzimidazol-1-yl]methyl]-2-furanmethanol ethanedioate (1:3); mp. 203.5° C. (comp. 1.24).

EXAMPLE 23

A mixture of 3.4 parts of compound (1.21), 0.82 parts of sodium acetate and 73.5 parts of acetic acid was stirred for 4 hours at reflux temperature. The reaction mixture was evaporated and the residue was taken up in water. After basifying with $K_2CO_3$, the solution was extracted with dichloromethane and the extract was dried, filtered and evaporated. To the residue there were added 3.5 parts of potassium hydroxide and 39 parts of 2-propanol and the whole was stirred for 3 hours at reflux temperature. The solvent was evaporated and water was added to the residue. The product was extracted with 1-butanol and the extract was dried, filtered and evaporated. The residue was purified by column chromatography (silica gel; CH₂Cl₂/CH₃OH(NH₃) 90:10). The eluent of the desired fraction was evaporated and the residue was converted into the ethanedioate (2:5) salt in ethanol. The product was filtered off and dried, yielding 2.20 parts (45.7%) of 6-[[2-[4-[[1-[[5-(hydroxymethyl)-2-furanyl]-methyl]-1H-benzimidazol-2-yl]methyl]-1-piperidinyl]ethyl]amino]-3(2H)-pyridazinone ethanedioate (2:5); mp. 210.2° C. (comp. 1.25).

EXAMPLE 24

A mixture of 22.4 parts of intermediate (15), 13 parts of mercury(II)oxide, a spoonful of sulfur and 178 parts of tetrahydrofuran was stirred for 3 hours at reflux temperature. The reaction mixture was filtered and the filtrate was evaporated. The residue was partitioned between $H_2SO_4$ and dichloromethane. The organic layer was dried, filtered and evaporated and the residue was purified by column chromatography (silica gel; CH₂Cl₂/C₂H₅OH 95:5). The eluent of the desired fraction was evaporated, yielding 9.9 parts (47.9%) of ethyl hexahydro-4-[[3-[[5-(hydroxymethyl)-2-furanyl]methyl]-3H-imidazo[4,5-b]pyridin-2-yl]amino]-1H-azepine-1-carboxylate (comp. 4.04).

All new compounds listed in Tables 1 to 6 were prepared following the procedures described hereinabove. For each compound the actually used procedure is referred to in the column captioned by "Ex. No.".

TABLE 1

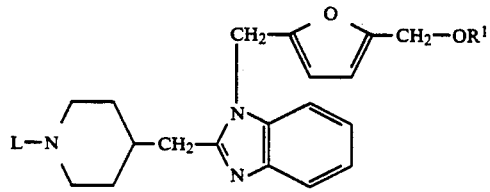

| Co. No. | Ex. No. | R¹ | L | Physical data-mp. |
|---|---|---|---|---|
| 1.01 | 8a | H— | C₆H₅—CH₂— | 143.8° C. |
| 1.02 | 7e | CH₃—CO— | C₆H₅—CH₂— | — |
| 1.03 | 8c | CH₃—CO— | C₂H₅OOC— | — |
| 1.04 | 8d | H— | H— | — |
| 1.05 | 8d | C₆H₅—CH₂— | H— | — |
| 1.06 | 7c | C₆H₅—CH₂— | 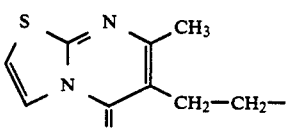 | 180.5° C./1/2H₂O/3/2* |
| 1.07 | 7c | H— | 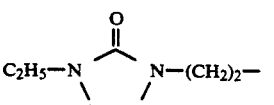 | 124.8° C. |
| 1.08 | 7c | H— | 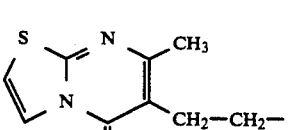 | 159.7° C. |
| 1.09 | 7c | H— | 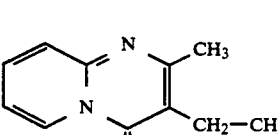 | 145.0° C./H₂O |

TABLE 1-continued

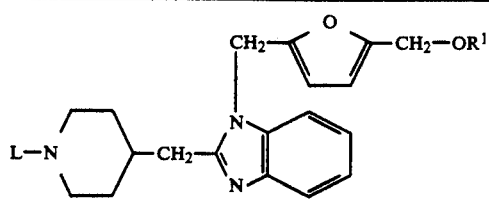

| Co. No. | Ex. No. | R¹ | L | Physical data-mp. |
|---|---|---|---|---|
| 1.10 | 7c | H— | (structure: thiazine-pyrimidinone with CH₃, CH₂—CH₂—) | 183.0° C. |
| 1.11 | 7c | H— | 4-CH₃O—C₆H₄—(CH₂)₂— | 189.7° C./1/2C₂H₅OH/* |
| 1.12 | 7c | H— | iC₃H₇—NH—CO—(CH₂)₂— | 135.0° C. |
| 1.13 | 7c | H— | NC—CH₂— | — |
| 1.14 | 7d | H— | H₂N—(CH₂)₂— | — |
| 1.15 | 7e | H— | (N-methylpyrrole-2-carboxamide)—NH—(CH₂)₂— | 176.3° C./2(COOH)₂/1/2H₂O |
| 1.16 | 7e | H— | (furan-2-carboxamide)—NH—(CH₂)₂— | 137.4° C./2(COOH)₂/H₂O |
| 1.17 | 8e | H— | CH₃— | 158.1° C. |
| 1.18 | 7c | H— | 4F—C₆H₄—CO—(CH₂)₃— | 120.0° C. 2(c-C₆H₁₁—NHSO₃H) |
| 1.19 | 14 | H— | (isoxazole-pyrimidinone with CH₃, CH₃, CH₂—CH₂—) | 87.3° C. |
| 1.20 | 12 | H— | HO—CH₂—CH₂— | 1/2*/227.8° C. |
| 1.21 | 17 | H— | (6-chloropyridazin-3-yl)—NH—(CH₂)₂— | 188.4° C. |
| 1.22 | 17 | H— | (pyrazin-2-yl)—NH—(CH₂)₂— | */184.2° C. |
| 1.23 | 18 | H— | (pyrimidin-2-yl)—NH—(CH₂)₂— | 111.5° C. |
| 1.24 | 22 | H— | (pyridazin-3-yl)—NH—(CH₂)₂— | 3(COOH)₂/203.5° C. |
| 1.25 | 23 | H— | (6-oxo-1,6-dihydropyridazin-3-yl)—NH—(CH₂)₂— | 5/2(COOH)₂/210.2° C. |

TABLE 1-continued

Structure: L—N(piperidine)—CH₂—[benzimidazole with N-CH₂-furan-CH₂-OR¹ substituent]

| Co. No. | Ex. No. | R¹ | L | Physical data-mp. |
|---|---|---|---|---|
| 1.26 | 7e | H— | 2-amino-benzamide-NH-(CH₂)₂— | — |

*(E)-2-butenedioate

TABLE 2

Structure: L—N(piperidine)—B—[imidazopyridine with N-CH₂-furan-CH₂-OR¹ substituent]

| Co. No. | Ex. No. | B | R¹ | L | Physical data-mp. |
|---|---|---|---|---|---|
| 2.01 | 9 | NH | H— | $C_2H_5$—OOC— | 148.3° C. |
| 2.02 | 7b | NH | H— | H— | 220.2° C./3/2* |
| 2.03 | 7b | NH | H— | H— | 124.8° C./1/2H₂O |
| 2.04 | 7c | NH | H— | 4-$CH_3O$—$C_6H_4$—$(CH_2)_2$— | 111.0° C./H₂O |
| 2.05 | 7c | NH | H— | $C_2H_5$—O—$(CH_2)_2$— | 105.8° C./1/2H₂O |
| 2.06 | 7c | NH | H— | 4-F—$C_6H_4$—CO—$(CH_2)_3$— | 200.5° C./(COOH)₂ |
| 2.07 | 7c | NH | H— | 2,3-dihydro-benzimidazolone-N-(CH₂)₂— | 231.3° C. |
| 2.08 | 7c | NH | H— | thiazolopyrimidinone-CH₂-CH₂— | 250.0° C./H₂O |
| 2.09 | 7c | NH | H— | thiazolopyrimidinone-CH₂-CH₂— | 239.0° C. |
| 2.10 | 15 | NH | H— | pyrido-pyrimidinone-CH₂-CH₂— | 177.7° C./2H₂O/5/2* |
| 2.11 | 10 | CH₂ | H— | $C_6H_5$—$CH_2$— | 115.4° C. |
| 2.12 | 10 | CH₂ | $CH_3$— | $C_6H_5$—$CH_2$— | 201.5° C./(COOH)₂ |
| 2.13 | 10 | CH₂ | H— | $C_2H_5OOC$— | — |
| 2.14 | 7b | CH₂ | H— | H— | 151.9° C./H₂O/2* |

TABLE 2-continued

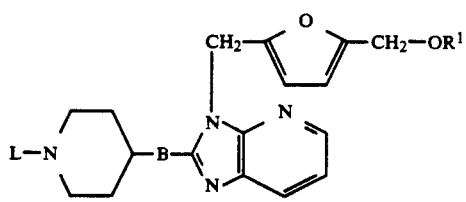

| Co. No. | Ex. No. | B | R¹ | L | Physical data-mp. |
|---|---|---|---|---|---|
| 2.15 | 15 | $CH_2$ | H— | [thiazine-pyrimidinone with $CH_2$-$CH_2$—] | 203.3° C./* |
| 2.16 | 14 | NH | H— | $C_2H_5$—N, triazinone, N—$(CH_2)_2$— | 173.1° C. |
| 2.17 | 14 | NH | H— | i-$C_3H_7$—NHCO—$C_2H_4$— | 175.3° C./3/2(COOH)$_2$ |
| 2.18 | 8e | NH | H— | $CH_3$— | 183.3° C. |
| 2.19 | 12 | NH | H— | 4F—$C_6H_4$—O$CH_2$—CHOH—$CH_2$— | 161.6° C. |
| 2.20 | 7c | $CH_2$ | H— | furan-2-carboxamide-NH—$(CH_2)_2$— | 174.7° C. |
| 2.21 | 7e | NH | H— | furan-2-carboxamide-NH—$(CH_2)_2$— | 175.9° C. |
| 2.22 | 14 | $CH_2$ | H— | [thiazolo-pyrimidinone with $CH_2$—$CH_2$—] | 163.7° C. |
| 2.23 | 7c | $CH_2$ | H— | 4F—$C_6H_4$—CO—$(CH_2)_3$— | 174.6° C./ (c-$C_6H_{11}$—NHSO$_3$H) |
| 2.24 | 7c | $CH_2$ | H— | NC—$CH_2$— | — |
| 2.25 | 7d | $CH_2$ | H— | $H_2N$—$(CH_2)_2$— | — |
| 2.26 | 15 | NH— | H— | NC—$CH_2$— | — |
| 2.27 | 7d | NH— | H— | $H_2N$—$(CH_2)_2$— | — |
| 2.28 | 7b | $CH_2$ | H— | H— | 137.6° C. |
| 2.29 | 14 | $CH_2$ | H— | [isoxazolo-pyrimidinone with $CH_2$—$CH_2$—] | $H_2O$/91.2° C. |
| 2.30 | 7e | NH— | H— | [1-methylindole-2-carboxamide-NH—$(CH_2)_2$—] | 177.5° C. |
| 2.31 | 14 | $CH_2$ | H— | [pyrido-pyrimidinone with $(CH_2)_2$—] | 178.4° C. |

TABLE 2-continued

Structure:

![Structure: L-N-piperidine-B-imidazo[4,5-b]pyridine with N-CH2-furan-CH2-OR1]

| Co. No. | Ex. No. | B | R¹ | L | Physical data-mp. |
|---|---|---|---|---|---|
| 2.32 | 14 | NH— | H— | [isoxazole-methyl fused structure with CH3 groups and -CH2-CH2-] | 202.5° C. |
| 2.33 | 14 | CH2 | H— | [thiazine-pyrimidinone structure with CH3 and -(CH2)2-] | H2O/159.5° C. |
| 2.34 | 17 | CH2 | H— | [9-methylpurine-NH-(CH2)2-] | 1/2H2O/145.3° C. |
| 2.35 | 16 | CH2 | H— | [pyridin-2-yl-(CH2)2-] | 3/2*/159.8° C. |
| 2.36 | 7e | CH2 | H— | [thiophene-2-C(=O)-NH-(CH2)2-] | 174.7° C. |
| 2.37 | 7e | CH2 | H— | [3-aminopyrazine-2-C(=O)-NH-(CH2)2-] | 133.0° C. |
| 2.38 | 21 | CH2 | H— | C2H5—NH—CO—NH—(CH2)2— | 119.7° C. |

*(E)-2-butenedioate

TABLE 3

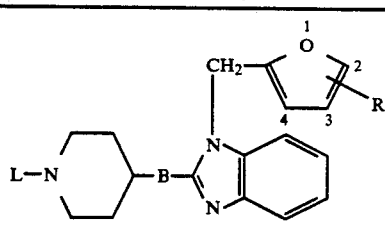

| Co. No. | Ex. No. | B | R | L | Physical data-mp. |
|---|---|---|---|---|---|
| 3.01 | 8a | NH— | 2-CH2OH | 4-CH3O—C6H4—(CH2)2— | 110.1° C. |
| 3.02 | 8a | NH— | 3-CH2OH | 4-CH3O—C6H4—(CH2)2— | 136.1° C. |
| 3.03 | 8a | NH— | 2-CH2OH | CH3— | 124.1° C./1/2H2O |
| 3.04 | 8a | NH— | 3-CH2OH | CH3— | 133.3° C./1/2H2O |
| 3.05 | 7a | NH— | 2-CH2OH | C2H5—OOC— | 141.6° C. |
| 3.06 | 11 | NH— | 2-CH2OCH3 | C2H5—OOC— | — |
| 3.07 | 7b | NH— | 2-CH2OCH3 | H— | 240.8° C./2* |

TABLE 3-continued

[Structure: benzimidazole with furan-CH2 substituent (positions 1-O, 2, 3-R, 4), B linking to piperidine-N-L]

| Co. No. | Ex. No. | B | R | L | Physical data-mp. |
|---|---|---|---|---|---|
| 3.08 | 7c | NH— | 2-CH₂OCH₃ | 4-CH₃O—C₆H₄—(CH₂)₂— | 201.3° C./2* |
| 3.09 | 7c | NH— | 2-CH₂OCH₃ | [pyrido-pyrimidinone with CH₃ and CH₂—CH₂—] | 181.7° C./3/2H₂O/2* |
| 3.10 | 7c | NH— | 2-CH₂OCH₃ | [thiazolo-pyrimidinone with CH₃ and CH₂—CH₂—] | 159.6° C./H₂O/2* |
| 3.11 | 7b | NH— | 2-CH₂OH | H— | 156.3° C. |
| 3.12 | 21 | NH— | 2-CH₂OH | iC₃H₇—NH—CO—(CH₂)₂— | 139.7° C. |
| 3.13 | 7c | NH— | 2-CH₂OH | [H₃C—CH₂—N tetrazinone N—(CH₂)₂—] | 163.1° C. |
| 3.14 | 7c | NH— | 2-CH₂OH | [thiazolo-pyrimidinone with CH₃ and CH₂—CH₂—] | 208.8° C. |
| 3.15 | 7c | NH— | 2-CH₂OH | [dihydrothiazolo-pyrimidinone with CH₃ and CH₂—CH₂—] | 210.4° C./H₂O |
| 3.16 | 7c | NH— | 2-CH₂OH | C₂H₅—O—(CH₂)₂— | 177.0° C./2(COOH)₂ |
| 3.17 | 7c | NH— | 2-CH₂OH | [dihydropyrido-pyrimidinone with CH₃ and CH₂—CH₂—] | 237.0° C./1/2H₂O |
| 3.18 | 7c | NH— | 2-CH₂OH | 4F—C₆H₄—CO—(CH₂)₃— | 134.8° C. |
| 3.19 | 7c | NH— | 2-CH₂OH | [benzimidazolinone—N—(CH₂)₂—] | 206.8° C. |
| 3.20 | 12 | NH— | 2-CH₂OH | 4F—C₆H₄—O—CH₂—CHOH—CH₂— | 136.8° C. |
| 3.21 | 13 | NH— | 2-CH₂OH | CH₃—CO— | 213.9° C. |
| 3.22 | 7c | NH— | 2-CH₂OH | NC—CH₂— | 209.8° C. |
| 3.23 | 7d | NH— | 2-CH₂OH | H₂N—(CH₂)₂— | 164.6° C. |

TABLE 3-continued

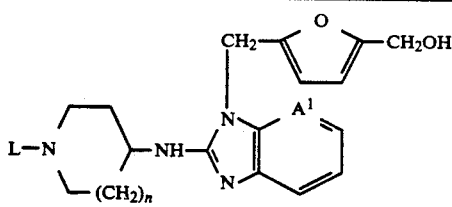

| Co. No. | Ex. No. | B | R | L | Physical data-mp. |
|---|---|---|---|---|---|
| 3.24 | 7e | NH— | 2-CH₂OH | [1-methylpyrrole-2-carboxamide-N-(CH₂)₂—] | 182.2° C. |
| 3.25 | 7e | NH— | 2-CH₂OH | [furan-2-carboxamide-N-(CH₂)₂—] | 200.2° C. |
| 3.26 | 18 | NH— | 2-CH₂OH | [3-nitropyridin-4-yl-NH-(CH₂)₂—] | 191.0° C. |
| 3.27 | 7c | NH— | 2-CH₂OH | [isoxazole-pyrimidinone-CH₂-CH₂—] | 206.2° C./1/2H₂O |
| 3.28 | 8a | NH— | 3-CH₂OH | H₅C₂O(CH₂)₂— | 118.0° C./H₂O |
| 3.29 | 8a | NH— | 4-CH₂OH | (4-CH₃OC₆H₄)—CH₂—CH₂— | 137.7° C. |
| 3.30 | 20 | NH— | 4-CH₂OH | CH₃ | 205.4° C. |
| 3.31 | 14 | NH— | 2-CH₂OH | [thiazine-pyrimidinone-(CH₂)₂—] | 226.9° C. |
| 3.32 | 24 | NH— | 2-CH(OH)CH₃ | CH₃ | 187.6° C./3/2* |
| 3.34 | 20 | NCH₃ | 2-CH₂OH | CH₃ | 185.1° C./3/2* |
| 3.35 |  | O | 2-CH₂OH | CH₃ | — |
| 3.36 |  | S | 2-CH₂OH | CH₃ | — |

*(E)-2-butenedioate

TABLE 4

| Co. No. | Ex. No. | n | A¹ | L | Physical data-mp. |
|---|---|---|---|---|---|
| 4.01 | 7a | 2 | CH— | C₂H₅OOC | 176.8° C. |
| 4.02 | 20 | 2 | CH— | CH₃— | 119.7° C. |
| 4.03 | 7b | 2 | CH— | H— | 203.4° C./2* |
| 4.04 | 24 | 2 | N | H₅C₂OOC— | — |
| 4.05 | 7b | 2 | N | H— | 167.6° C./2* |

TABLE 4-continued

[Structure shown with L-N-piperidine-(CH2)n-NH linked to imidazo[A1]pyridine with N-CH2-furan-CH2OH substituent]

| Co. No. | Ex. No. | n | A¹ | L | Physical data-mp. |
|---|---|---|---|---|---|
| 4.06 | 14 | 2 | CH— | [2-(3-methyl-4-oxo-4H-pyrido[1,2-a]pyrimidin-3-yl)(CH₂)₂—] | 169.0° C. |
| 4.07 | 14 | 2 | CH— | (CH₃)₂CH—NH—C(O)—(CH₂)₂— | 184.9° C./1/2H₂O  2(c.C₆H₁₁NHSO₃H) |
| 4.08 | 14 | 2 | CH— | [2-oxo-oxazolidin-3-yl-(CH₂)₂—] | 174.8° C./2*/1/2H₂O |
| 4.09 | 14 | 2 | CH— | (4-CH₃O—C₆H₄)—(CH₂)₂— | 148.6° C./2* |
| 4.10 | 7c | 2 | CH— | NC—CH₂— | 157.3° C. |
| 4.11 | 7d | 2 | CH— | H₂N—(CH₂)₂— | — |
| 4.12 | 7e | 2 | CH— | [furan-2-yl-C(O)—NH—(CH₂)₂—] | 167.3° C. |
| 4.13 | 14 | 2 | CH— | [2-(6-methyl-7-oxo-7H-thiazolo[3,2-a]pyrimidin-5-yl)(CH₂)₂—] | 185.2° C./1/2H₂O  2(c.C₆H₁₁NHSO₃H) |
| 4.14 | 19 | 2 | CH— | [3-(4-nitropyridin-3-yl)NH—(CH₂)₂—] | 155.1° C./1/2H₂O |
| 4.15 | 14 | 2 | CH— | [2-(6-methyl-7-oxo-2,3-dihydro-7H-thiazolo[3,2-a]pyrimidin-5-yl)(CH₂)₂—] | 177.1° C. |
| 4.16 | 8e | 2 | N | CH₃ | 175.9° C./2*/1/2H₂O |
| 4.17 | 20 | 0 | CH— | CH₃ | 133.1° C. |

TABLE 5

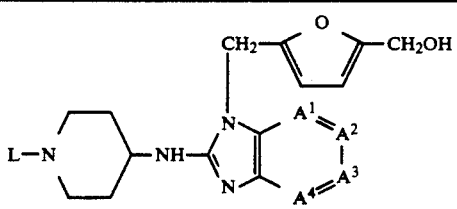

| Comp. No. | Ex. No. | —A¹—A²—A³—A⁴— | L | Physical data |
|---|---|---|---|---|
| 5.01 | 24 | —N=CH—N=CH— | H₅C₂OOC— | 166.7° C. |

TABLE 5-continued

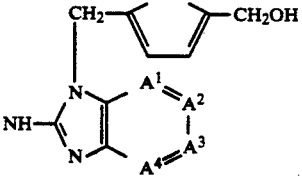

| Comp. No. | Ex. No. | —A¹—A²—A³—A⁴— | L | Physical data |
|---|---|---|---|---|
| 5.02 | 7b | —N=CH—N=CH— | H— | 160.1° C./H$_2$O |
| 5.03 | 14 | —N=CH—N=CH— | 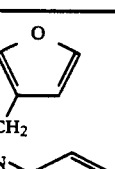 | 160.8° C./H$_2$O |
| 5.04 | 8e | —N=CH—N=CH— | CH$_3$— | 191.3° C. |
| 5.05 | 24 | —CH=CH—N=CH— | H$_5$C$_2$OOC— | 176.1° C. |
| 5.06 | 7b | —CH=CH—N=CH— | H— | — |
| 5.07 | 8e | —CH=CH—N=CH— | CH$_3$— | 188.4° C. |
| 5.08 | 8e | —CH=N—CH=CH— | CH$_3$— | |
| 5.09 | 7b | —CH=CH—CH=N— | H— | 207.7° C. |
| 5.10 | 8e | —CH=CH—CH=N— | CH$_3$— | 172.5° C./H$_2$O |

TABLE 6

| Comp. No. | Ex. No. | L | Physical data |
|---|---|---|---|
| 6.01 | 20 | CH$_3$— | 142.8° C. |
| 6.02 | 8a | (4-CH$_3$O—C$_6$H$_4$)—(CH$_2$)$_2$— | 141.1° C. |

C. PHARMACOLOGICAL EXAMPLE

EXAMPLE 25

The useful antihistaminic properties of the compounds of formula (I) can be demonstrated in the test "Protection of rats from compound 48/80-induced lethality", which is described in U.S. Pat. No. 4,556,660, incorporated herein by reference, and the results of which are given in Table 7 below. The term (sc) signifies subcutaneous administration.

TABLE 7

| Co. No. | ED$_{50}$ (mg/kg): compound 48/80 induced lethality in rats. |
|---|---|
| 1.07 | 0.04 (sc) |
| 1.08 | 0.01 (sc) |
| 1.09 | 0.02 (sc) |
| 1.10 | 0.01 (sc) |
| 1.11 | 0.04 (sc) |
| 1.12 | 0.01 (sc) |
| 1.15 | 0.04 (sc) |
| 1.17 | 0.04 (sc) |
| 1.22 | 0.04 (sc) |
| 1.23 | 0.02 (sc) |
| 1.24 | 0.02 (sc) |
| 1.25 | 0.01 (sc) |
| 2.09 | 0.01 (sc) |
| 2.10 | 0.04 (sc) |
| 2.11 | 0.04 (sc) |
| 2.16 | 0.04 (sc) |
| 2.18 | 0.01 (sc) |
| 2.20 | 0.04 (sc) |
| 2.22 | 0.04 (sc) |
| 2.23 | 0.04 (sc) |
| 2.32 | 0.02 (sc) |
| 2.33 | 0.04 (sc) |
| 2.35 | 0.02 (sc) |
| 3.03 | 0.02 (sc) |
| 3.11 | 0.04 (sc) |
| 3.12 | 0.04 (sc) |
| 3.13 | 0.04 (sc) |
| 3.15 | 0.04 (sc) |
| 3.17 | 0.04 (sc) |
| 3.19 | 0.02 (sc) |
| 3.22 | 0.04 (sc) |
| 3.25 | 0.02 (sc) |
| 3.26 | 0.04 (sc) |
| 3.31 | 0.04 (sc) |
| 4.05 | 0.02 (sc) |
| 4.07 | 0.04 (sc) |
| 4.12 | 0.04 (sc) |
| 4.14 | 0.04 (sc) |
| 4.16 | 0.02 (sc) |
| 5.03 | 0.04 (sc) |
| 5.04 | 0.02 (sc) |

D. COMPOSITION EXAMPLES

EXAMPLE 26

ORAL DROPS 500 grams of the A.I. was dissolved in 0.5 of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 27

ORAL SOLUTION

Grams of methyl 4-hydroxybenzoate and 1 part of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 28

CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

EXAMPLE 29

FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 ml of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10.000 tablets, each containing 10 mg of the active ingredient.

Coating

To a solution of 10 grams methyl cellulose (Methocel 60 HG ®) in 75 ml of denaturated ethanol there was added a solution of 5 grams of ethyl cellulose (Ethocel 22 cps ®) in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension (Opaspray K-1-2109 ®) and the whole was homogenated. The tablet cores were coated with the thus obtained mixture in a coating apparatus.

EXAMPLE 30

INJECTABLE SOLUTION 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration (U.S.P. XVII p. 811) and filled in sterile containers.

EXAMPLE 31

SUPPOSITORIES

3 Grams A.I. was dissolved in a solution of 3 grams 2,3-dihydroxybutanedioic acid in 25 ml polyethylene glycol 400. 12 Grams surfactant (SPAN ®) and triglycerides (Witepsol 555 ®) q.s. ad 300 Grams were molten together. The latter mixture was mixed well with the former solution. The thus obtained mixture was poured into moulds at a temperature of 37°-38° C. to form 100 suppositories each containing 30 mg/ml of the A.I.

EXAMPLE 32

INJECTABLE SOLUTION

60 Grams of A.I. and 12 grams of benzylalcohol were mixed well and sesame oil was added q.s. ad 1 l, giving a solution comprising 60 mg/ml of A.I. The solution was sterilized and filled in sterile containers.

We claim:

1. A compound of the formula:

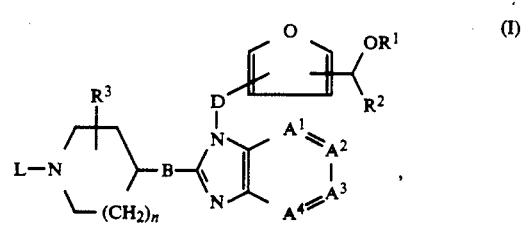

a pharmaceutically acceptable acid addition salt thereof or a stereochemically isomeric form thereof, wherein:
—$A^1$=$A^2$—$A^3$=$A^4$— represents a bivalent radical having the formula:

—N=CH—CH=CH— (a-2), wherein one or two hydrogen atoms in said radical (a-2) each independently from one another may be replaced by halo, $C_{1-6}$alkyl, $C_{1-6}$alkyloxy, trifluoromethyl or hydroxy;
D represents $C_{1-4}$alkanediyl;
$R^1$ represents hydrogen, $C_{1-6}$alkyl, aryl$C_{1-6}$alkyl, or $C_{1-6}$alkylcarbonyl;
$R^2$ represents hydrogen or $C_{1-6}$alkyl;
$R^3$ represents hydrogen or $C_{1-6}$alkyl;
n represents 1;
B represents NH; and
L represents a radical of the formula:

—Alk—$R^5$ (b-1);

wherein:

$R^5$ represents a bicyclic radical of the formula:

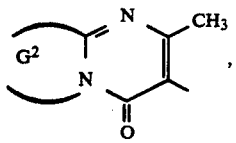  (c-4-a)

wherein $G^2$ represents —CH=CH—CH=CH—, —S—(CH$_2$)$_2$—, —S—CH=CH—, or —CH=C(CH$_3$)—O—; and Alk represents $C_{1-6}$alkanediyl.

2. The compound of claim 1 wherein $R^1$ represents hydrogen or aryl$C_{1-6}$alkyl, $R^3$ represents hydrogen, and the moiety:

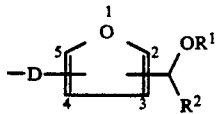

represents (2-CHR$^2$OR$^1$-furan-5-yl)$C_{1-4}$alkyl or (3-CHR$^2$OR$^1$-furan-5-yl)$C_{1-4}$alkyl.

3. A compound according to claim 2 wherein $R^1$ represents hydrogen, and $R^2$ represents hydrogen.

4. A compound according to claim 3 wherein said compound is 6-[2-[4[[3-[[5-(hydroxymethyl)-2-furanyl]-methyl]-3H-imidazo[4,5-b]pyridin-2-yl]amino]-1-piperidinyl]ethyl]-7-methyl-5H-thiazolo[3,2-a]pyrimidin-5-one.

5. An antiallergic composition comprising a pharmaceutically acceptable carrier and as active ingredient an antiallergically effective amount of a compound as claimed in claim 1.

6. A method of treating warm-blooded animals suffering from allergic diseases comprising administering to said warm-blooded animals an antiallergically effective amount of a compound as claimed in claim 1.

* * * * *